United States Patent
Bissett et al.

(10) Patent No.: US 6,284,802 B1
(45) Date of Patent: *Sep. 4, 2001

(54) METHODS FOR REGULATING THE CONDITION OF MAMMALIAN KERATINOUS TISSUE

(75) Inventors: Donald Lynn Bissett, Hamilton; Elizabeth Ann Jewell-Motz, Cincinnati, both of OH (US)

(73) Assignee: The Procter & Gamble Company, Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 122 days.

(21) Appl. No.: 09/541,965

(22) Filed: Apr. 4, 2000

Related U.S. Application Data

(60) Provisional application No. 60/129,975, filed on Apr. 19, 1999.

(51) Int. Cl.[7] .................. A61K 31/045; A61K 31/04; A61K 38/00; A61K 31/60; A61K 31/44
(52) U.S. Cl. ............... 514/739; 514/2; 514/159; 514/356; 514/725
(58) Field of Search .................... 514/739, 356, 514/725, 159, 2

(56) References Cited

U.S. PATENT DOCUMENTS

| | | | |
|---|---|---|---|
| 4,331,655 | 5/1982 | Tur | 424/59 |
| 4,496,536 | 1/1985 | Möller et al. | 424/70 |
| 4,520,029 | * 5/1985 | Tomiyama | 514/479 |
| 5,415,861 | 5/1995 | Duffy et al. | 424/401 |
| 5,466,718 | 11/1995 | Nakatsu et al. | 514/724 |
| 5,472,684 | * 12/1995 | Nabi et al. | 424/49 |
| 5,472,699 | 12/1995 | Duffy et al. | 424/401 |
| 5,698,206 | * 12/1997 | Becker et al. | 424/401 |
| 5,753,610 | 5/1998 | Harada et al. | 512/25 |

FOREIGN PATENT DOCUMENTS

| | | | |
|---|---|---|---|
| 680565 | 9/1992 | (CH) | A61K/7/48 |
| 1131549 | 9/1996 | (CN) | A61K/35/78 |
| 3147911 | 6/1982 | (DE) | A61K/7/48 |
| 4125871 | 3/1993 | (DE) | A61K/31/355 |
| 4400843 | 7/1995 | (DE) | C07D/339/04 |
| 4411664 | 10/1995 | (DE) | A61K/7/32 |
| 0 447318 | 9/1991 | (EP) | A61K/9/51 |
| 0 467795 | 1/1992 | (EP) | A61K/31/07 |
| 0 659755 | 6/1995 | (EP) | C07F/9/10 |
| 0 684299 | 11/1995 | (EP) | C11B/9/00 |
| 0 729747 | 9/1996 | (EP) | A61K/7/48 |
| 0 773209 | 5/1997 | (EP) | C07C/69/587 |
| 2285804 | 8/1998 | (GB) | C07C/69/007 |
| 10-167957 | 6/1993 | (JP) | A61K/31/045 |
| 5-229962 | 9/1993 | (JP) | A61K/47/16 |
| 6-128120 | 5/1994 | (JP) | A61K/7/48 |
| 6-128137 | 5/1994 | (JP) | A61K/7/48 |
| 7-118145 | 5/1995 | (JP) | A61K/31/045 |
| 9-071525 | 3/1997 | (JP) | A61K/31/015 |
| 9-071526 | 3/1997 | (JP) | A61K/31/12 |
| 9-077660 | 3/1997 | (JP) | A61K/31/045 |
| 10-114648 | 5/1998 | (JP) | A61K/31/045 |
| 10-158194 | 6/1998 | (JP) | A61K/47/08 |
| WO 97/48387 | 12/1997 | (WO) | A61K/9/70 |
| WO 98/00168 | 1/1998 | (WO) | A61K/45/06 |
| WO 98/32444 | 7/1998 | (WO) | A61K/31/56 |
| WO 98/42309 | 10/1998 | (WO) | A61K/7/48 |

OTHER PUBLICATIONS

Single ingredient in product query—Farnesol (no date available).
Borlind of Germany, www.borlind.com/artofmnthoct98.html/—Article of the month: Farnesol, Oct. 1998.
Natures Own USA, www.naturesownusa.com/skincare-.html/—Written description of Day Cream product, Mar. 1999.
Hydron Technologies, www.hydron.com/skincare–oil2.html/—Written description of Hydron Oil Balancing Serum, Apr. 1999.

\* cited by examiner

*Primary Examiner*—Raymond Henley, III
(74) *Attorney, Agent, or Firm*—Dara M. Kendall; Fumiko Tsuneki; Michael E. Hilton

(57) ABSTRACT

The present invention relates to methods for regulating the condition of mammalian keratinous tissue wherein the methods comprise the step of topically applying to the keratinous tissue of a mammal needing such treatment, a safe and effective amount of a composition comprising:

a) a safe and effective amount of farnesol; and b) a dermatologically-acceptable carrier for the farnesol.

In additional embodiments, the above composition is suitable for thickening skin and preventing and/or retarding atrophy of mammalian skin, preventing and/or retarding the appearance of spider vessels and/or red blotchiness on mammalian skin, preventing and/or retarding the appearance of dark circles under the eye of a mammal, preventing and/or retarding sallowness of mammalian skin, preventing and/or retarding sagging of mammalian skin, softening and/or smoothing lips, hair and nails of a mammal, and preventing and/or relieving itch of mammalian skin.

25 Claims, No Drawings

SEQUENCE LISTING

```
<160> NUMBER OF SEQ ID NOS: 2

<210> SEQ ID NO 1
<211> LENGTH: 5
<212> TYPE: PRT
<213> ORGANISM: Artificial Sequence
<220> FEATURE:
<221> NAME/KEY: UNSURE
<222> LOCATION: (1)..(5)
<223> OTHER INFORMATION: Commercially available pentapeptide
<220> FEATURE:
<223> OTHER INFORMATION: Description of Artificial Sequence:
      palmitoyl - lys-thr-thr-lys-ser

<400> SEQUENCE: 1

Lys Thr Thr Lys Ser
  1               5

<210> SEQ ID NO 2
<211> LENGTH: 4
<212> TYPE: PRT
<213> ORGANISM: Artificial Sequence
<220> FEATURE:
<221> NAME/KEY: UNSURE
<222> LOCATION: (1)..(4)
<223> OTHER INFORMATION: Commercially available tetrapeptide
<220> FEATURE:
<223> OTHER INFORMATION: Description of Artificial Sequence:
      arg-ser-arg-lys

<400> SEQUENCE: 2

Arg Ser Arg Lys
```

METHODS FOR REGULATING THE CONDITION OF MAMMALIAN KERATINOUS TISSUE

CROSS REFERENCE TO RELATED APPLICATION

This application claims the benefit of U.S. provisional patent application Ser. No. 60/129,975 filed on Apr. 19, 1999 in the names of Bissett et al.

TECHNICAL FIELD

The present invention relates to methods of regulating the condition of mammalian keratinous tissue using farnesol wherein the methods include: a) thickening skin and preventing and/or retarding atrophy in mammalian skin, b) preventing and/or retarding the appearance of spider vessels and/or red blotchiness on mammalian skin, c) preventing and/or retarding the appearance of dark circles under the eye of a mammalian, d) preventing and/or retarding sallowness of mammalian skin, e) preventing and/or retarding sagging of mammalian skin, f) softening and/or smoothing lips, hair and nails of a mammal, and g) preventing and/or relieving itch of mammalian skin. These methods are accomplished via the topical application of compositions containing farnesol to the keratinous tissue of a mammal needing such treatments.

BACKGROUND OF THE INVENTION

Currently, there are a number of personal care products which are available to consumers which are directed toward improving the health and physical appearance of human keratinous tissues such as the skin, hair, and nails which are equally useful for pet hygiene and grooming. The majority of these products are directed to delaying, minimizing or even eliminating skin wrinkling and other histological changes typically associated with the aging of skin or environmental damage to human skin.

Mammalian keratinous tissue, particularly human skin, is subjected to a variety of insults by both extrinsic and intrinsic factors. Such extrinsic factors include ultraviolet radiation, environmental pollution, wind, heat, infrared radiation, low humidity, harsh surfactants, abrasives, etc. Intrinsic factors, on the other hand, include chronological aging and other biochemical changes from within the skin. Whether extrinsic or intrinsic, these factors result in visible signs of skin damage. Typical skin damage includes thinning of the skin which occurs naturally as one ages. With such thinning, there is a reduction in the cells and blood vessels that supply the skin as well as a flattening of the dermal-epidermal junction which results in weaker mechanical resistance of this junction. See, for example, Oikarinen, "The Aging of Skin: Chronoaging Versus Photoaging," *Photodermatol. Photoimmunol. Photomed..* vol. 7, pp. 3–4, 1990. Other damage seen in aging or damaged skin includes spider vessels or red blotchiness, sallowness, sagging, under eye circles, and skin irritation which results in an itch. Additional damage incurred as a result of both external and internal factors includes damage to the keratinous tissue that constitutes lips, hair, and nails.

Therefore, there is a need for products and methods which seek to remedy these keratinous tissue conditions such that the condition of keratinous tissues like skin, hair, and nails are regulated.

It has now been surprisingly found that topical compositions which contain farnesol may be used to provide prophylactic as well as therapeutic treatments for these keratinous tissue conditions. For instance, it has been found that such compositions are useful for treating atrophy of the skin as well as sallowness, sagging, spider vessels, and itch relief. The compositions have also been found to be useful in smoothing and/or softening the keratinous tissue that constitutes the lips, hair, and nails.

SUMMARY OF THE INVENTION

The present invention relates to methods for regulating the condition of mammalian keratinous tissue wherein the methods each comprise the step of topically applying to the keratinous tissue of a mammal needing such treatment, a safe and effective amount of a composition comprising:

a) a safe and effective amount of farnesol; and b) a dermatologically-acceptable carrier for the farnesol.

In additional embodiments, the above composition is suitable for thickening skin and preventing and/or retarding atrophy of mammalian skin, preventing and/or retarding the appearance of spider vessels and/or red blotchiness on mammalian skin, preventing and/or retarding the appearance of dark circles under the eye of a mammal, preventing and/or retarding sallowness of mammalian skin, preventing and/or retarding sagging of mammalian skin, softening and/or smoothing lips, hair and nails of a mammal, and preventing and/or relieving itch of mammalian skin.

DETAILED DESCRIPTION OF THE INVENTION

All percentages and ratios used herein are by weight of the total composition and all measurements made are at 25° C., unless otherwise designated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

All publications cited herein are hereby incorporated by reference in their entirety.

The term "keratinous tissue," as used herein, refers to keratin-containing layers disposed as the outermost protective covering of mammals (e.g., humans, dogs, cats, etc.) which includes, but is not limited to, skin, lips, hair, toenails, fingernails, cuticles, hooves, etc.

The term "topical application", as used herein, means to apply or spread the compositions of the present invention onto the surface of the keratinous tissue.

The term "dermatologically-acceptable," as used herein, means that the compositions or components thereof so described are suitable for use in contact with mammalian keratinous tissue without undue toxicity, incompatibility, instability, allergic response, and the like.

The term "safe and effective amount" as used herein means an amount of a compound or composition sufficient to significantly induce a positive benefit, preferably a positive keratinous tissue appearance or feel benefit, including independently or in combinations the benefits disclosed herein, but low enough to avoid serious side effects, i.e., to provide a reasonable benefit to risk ratio, within the scope of sound judgment of the skilled artisan.

The term "sagging" as used herein means the laxity, slackness, or the like condition of skin that occurs as a result of loss of, damage to, alterations to, and/or abnormalities in dermal elastin.

The terms "smoothing" and "softening" as used herein mean altering the surface of the keratinous tissue such that its tactile feel is improved.

The compositions of the present invention are useful for topical application and for regulating keratinous tissue condition. Regulation of keratinous tissue condition, namely mammalian and in particular human skin condition, is often required due to conditions which may be induced or caused by factors internal and/or external to the body. For instance, "regulating skin condition" includes prophylactically regulating and/or therapeutically regulating skin condition, and may involve one or more of the following benefits: thickening of skin (i.e., building the epidermis and/or dermis and/or sub-dermal (e.g., subcutaneous fat or muscle) layers of the skin and where applicable the keratinous layers of the nail and hair shaft) to reduce skin atrophy, increasing the convolution of the dermal-epidermal border (also known as the rete ridges), preventing loss of skin elasticity (loss, damage and/or inactivation of functional skin elastin) such as elastosis, sagging, loss of skin recoil from deformation; non-melanin skin discoloration such as under eye circles, blotching (e.g., uneven red coloration due to, e.g., rosacea) (hereinafter referred to as "red blotchiness"), sallowness (pale color), discoloration caused by telangiectasia or spider vessels. As used herein, prophylactically regulating skin condition includes delaying, minimizing and/or preventing visible and/or tactile discontinuities in skin (e.g., texture irregularities in the skin which may be detected visually or by feel). As used herein, therapeutically regulating skin condition includes ameliorating, e.g., diminishing, minimizing and/or effacing, discontinuities in skin. Regulating skin condition involves improving skin appearance and/or feel.

As used herein, "regulating skin condition" is intended to include regulation of such signs irrespective of the mechanism of origin. For example, the mechanism can be from environmental damage, radiation exposure (including ultraviolet radiation), chronological aging, menopausal status (e.g., post-menopausal changes in skin), stress, diseases, etc.

The compositions of the present invention, including the essential and optional components thereof, are described in detail hereinafter.

Farnesol

The topical compositions of the present invention comprise a safe and effective amount of farnesol. Farnesol is a naturally occurring substance which is believed to act as a precursor and/or intermediate in the biosynthesis of squalene and sterols, especially cholesterol. Farnesol is also involved in protein modification and regulation (e.g., farnesylation of proteins), and there is a cell nuclear receptor which is responsive to farnesol.

Chemically, farnesol is [2E,6E]-3,7,11-trimethyl-2,6,10-dodecatrien-1-ol and as used herein "farnesol" includes isomers and tautomers of such. Farnesol is commercially available, e.g., under the names farnesol (a mixture from isomers from Dragoco, 10 Gordon Drive, Totowa, N.J.) and trans-trans-farnesol (Sigma Chemical Company, P.O. Box 14508, St. Louis, Mo.).

In the compositions of the present invention, farnesol preferably comprises from about 0.01% to about 99.99%, by weight of the composition, more preferably from about 0.01% to about 50%, even more preferably from about 0.1% to about 20%, still more preferably from about 0.2% to about 10%, and most preferably from about 0.5% to about 5%.

Dermatologically-Acceptable Carrier

The topical compositions of the present invention also comprise a dermatologically acceptable carrier for the farnesol. The phrase "dermatologically-acceptable carrier", as used herein, means that the carrier is suitable for topical application to the keratinous tissue, has good aesthetic properties, is compatible with the actives of the present invention and any other components, and will not cause any untoward safety or toxicity concerns. A safe and effective amount of carrier is from about 50% to about 99.99%, preferably from about 80% to about 99.9%, more preferably from about 90% to about 98%, and most preferably from about 90% to about 95% of the composition.

The carrier can be in a wide variety of forms. For example, emulsion carriers, including, but not limited to, oil-in-water, water-in-oil, water-in-oil-in-water, and oil-in-water-in-silicone emulsions, are useful herein.

Preferred carriers comprise an emulsion such as oil-in-water emulsions, water-in-oil emulsions, and water-in-silicone emulsions. As will be understood by the skilled artisan, a given component will distribute primarily into either the water or oil/silicone phase, depending on the water solubility/dispersibility of the component in the composition. Farnesol distributes primarily into the oil phase. Oil-in-water emulsions are especially preferred.

Emulsions according to the present invention generally contain a solution as described above and a lipid or oil. Lipids and oils may be derived from animals, plants, or petroleum and may be natural or synthetic (i.e., man-made). Preferred emulsions also contain a humectant, such as glycerin. Emulsions will preferably further contain from about 1% to about 10%, more preferably from about 2% to about 5%, of an emulsifier, based on the weight of the carrier. Emulsifiers may be nonionic, anionic or cationic. Suitable emulsifiers are disclosed in, for example, U.S. Pat. No. 3,755,560, issued Aug. 28, 1973, Dickert et al.; U.S. Pat. No. 4,421,769, issued Dec. 20, 1983, Dixon et al.; and *McCutcheon's Detergents and Emulsifiers*, North American Edition, pages 317–324 (1986).

The emulsion may also contain an anti-foaming agent to minimize foaming upon application to the keratinous tissue. Anti-foaming agents include high molecular weight silicones and other materials well known in the art for such use.

Suitable emulsions may have a wide range of viscosities, depending on the desired product form. Exemplary low viscosity emulsions, which are preferred, have a viscosity of about 50 centistokes or less, more preferably about 10 centistokes or less, most preferably about 5 centistokes or less.

Preferred water-in-silicone and oil-in-water emulsions are described in greater detail below.

a) Water-in-Silicone Emulsion

Water-in-silicone emulsions contain a continuous silicone phase and a dispersed aqueous phase.

(i) Continuous Silicone Phase

Preferred water-in-silicone emulsions of the present invention comprise from about 1% to about 60%, preferably from about 5% to about 40%, more preferably from about 10% to about 20%, by weight of a continuous silicone phase. The continuous silicone phase exists as an external phase that contains or surrounds the discontinuous aqueous phase described hereinafter.

The continuous silicone phase contains a polyorganosiloxane oil. A preferred water-in-silicone emulsion system is formulated to provide an oxidatively stable vehicle for the optional retinoid. The continuous silicone phase of these preferred emulsions comprises between about 50% and about 99.9% by weight of organopolysiloxane oil and less than about 50% by weight of a non-silicone oil. In an especially preferred embodiment, the continuous silicone phase comprises at least about 50%, preferably from about 60% to about 99.9%, more preferably from about 70% to about 99.9%, and even more preferably from about 80% to about 99.9%, polyorganosiloxane oil by weight of the continuous silicone phase, and up to about 50% non-silicone oils, preferably less about 40%, more preferably less than about 30%, even more preferably less than about 10%, and most preferably less than about 2%, by weight of the continuous silicone phase. These preferred emulsion systems provide more oxidative stability to the retinoid over extended periods of time than comparable water-in-oil emulsions containing lower concentrations of the polyorganosiloxane oil. Concentrations of non-silicone oils in the continuous silicone phase are minimized or avoided altogether so as to further enhance oxidative stability of the selected retinoid in the compositions. Water-in-silicone emulsions of this type are described in copending U.S. patent application Ser. No. 08/570,275, filed Dec. 11, 1995, in the names of Joseph Michael Zukowski, Brent William Mason, Larry Richard Robinson and Greg George Hillebrand.

The organopolysiloxane oil for use in the composition may be volatile, non-volatile, or a mixture of volatile and non-volatile silicones. The term "nonvolatile" as used in this context refers to those silicones that are liquid under ambient conditions and have a flash point (under one atmospheric of pressure) of or greater than about 100° C. The term "volatile" as used in this context refers to all other silicone oils. Suitable organopolysiloxanes can be selected from a wide variety of silicones spanning a broad range of volatilities and viscosities. Examples of suitable organopolysiloxane oils include polyalkylsiloxanes, cyclic polyalkylsiloxanes, and polyalkylarylsiloxanes.

Polyalkylsiloxanes useful in the composition herein include polyalkylsiloxanes with viscosities of from about 0.5 to about 1,000,000 centistokes at 25° C. Such polyalkylsiloxanes can be represented by the general chemical formula $R_3SiO[R_2SiO]_xSiR_3$ wherein R is an alkyl group having from one to about 30 carbon atoms (preferably R is methyl or ethyl, more preferably methyl; also mixed alkyl groups can be used in the same molecule), and x is an integer from 0 to about 10,000, chosen to achieve the desired molecular weight which can range to over about 10,000,000. Commercially available polyalkylsiloxanes include the polydimethylsiloxanes, which are also known as dimethicones, examples of which include the Vicasil® series sold by General Electric Company and the Dow Corning® 200 series sold by Dow Corning Corporation. Specific examples of suitable polydimethylsiloxanes include Dow Corning® 200 fluid having a viscosity of 0.65 centistokes and a boiling point of 100° C., Dow Corning® 225 fluid having a viscosity of 10 centistokes and a boiling point greater than 200° C., and Dow Corning® 200 fluids having viscosities of 50, 350, and 12,500 centistokes, respectively, and boiling points greater than 200° C. Suitable dimethicones include those represented by the chemical formula $(CH_3)_3SiO[(CH_3)_2SiO]_x[CH_3RSiO]_ySi(CH_3)_3$ wherein R is straight or branched chain alkyl having from two to about 30 carbon atoms and x and y are each integers of 1 or greater selected to achieve the desired molecular weight which can range to over about 10,000,000. Examples of these alkyl-substituted dimethicones include cetyl dimethicone and lauryl dimethicone.

Cyclic polyalkylsiloxanes suitable for use in the composition include those represented by the chemical formula $[SiR2—O]_n$ wherein R is an alkyl group (preferably R is methyl or ethyl, more preferably methyl) and n is an integer from about 3 to about 8, more preferably n is an integer from about 3 to about 7, and most preferably n is an integer from about 4 to about 6. When R is methyl, these materials are typically referred to as cyclomethicones. Commercially available cyclomethicones include Dow Corning® 244 fluid having a viscosity of 2.5 centistokes, and a boiling point of 172° C., which primarily contains the cyclomethicone tetramer (i.e. n=4), Dow Corning® 344 fluid having a viscosity of 2.5 centistokes and a boiling point of 178° C., which primarily contains the cyclomethicone pentamer (i.e. n=5), Dow Corning® 245 fluid having a viscosity of 4.2 centistokes and a boiling point of 205° C., which primarily contains a mixture of the cyclomethicone tetramer and pentamer (i.e. n=4 and 5), and Dow Corning® 345 fluid having a viscosity of 4.5 centistokes and a boiling point of 217°, which primarily contains a mixture of the cyclomethicone tetramer, pentamer, and hexamer (i.e. n=4, 5, and 6).

Also useful are materials such as trimethylsiloxysilicate, which is a polymeric material corresponding to the general chemical formula $[(CH_2)_3SiO_{1/2}]_x[SiO_2]y$, wherein x is an integer from about 1 to about 500 and y is an integer from about 1 to about 500. A commercially available trimethylsiloxysilicate is sold as a mixture with dimethicone as Dow Corning® 593 fluid.

Dimethiconols are also suitable for use in the composition. These compounds can be represented by the chemical formulas $R_3SiO[R_2SiO]_xSiR_2OH$ and $HOR_2SiO[R_2SiO]_xSiR_2OH$ wherein R is an alkyl group (preferably R is methyl or ethyl, more preferably methyl) and x is an integer from 0 to about 500, chosen to achieve the desired molecular weight. Commercially available dimethiconols are typically sold as mixtures with dimethicone or cyclomethicone (e.g. Dow Corning® 1401, 1402, and 1403 fluids).

Polyalkylaryl siloxanes are also suitable for use in the composition. Polymethylphenyl siloxanes having viscosities from about 15 to about 65 centistokes at 25° C. are especially useful.

Preferred for use herein are organopolysiloxanes selected from the group consisting, of polyalkylsiloxanes, alkyl substituted dimethicones, cyclomethicones, trimethylsiloxysilicates, dimethiconols, polyalkylaryl siloxanes, and mixtures thereof. More preferred for use herein are polyalkylsiloxanes and cyclomethicones. Preferred among the polyalkylsiloxanes are dimethicones.

As stated above, the continuous silicone phase may contain one or more non-silicone oils. Concentrations of non-silicone oils in the continuous silicone phase are preferably minimized or avoided altogether so as to further enhance oxidative stability of the selected retinoid in the compositions. Suitable non-silicone oils have a melting point of about 25° C. or less under about one atmosphere of pressure. Examples of non-silicone oils suitable for use in the continuous silicone phase are those well known in the chemical arts in topical personal care products in the form of water-in-oil emulsions, e.g., mineral oil, vegetable oils, synthetic oils, semisynthetic oils, etc.

(ii) Dispersed Aqueous Phase

The topical compositions of the present invention comprise from about 30% to about 90%, more preferably from about 50% to about 85%, and most preferably from about 70% to about 80% of a dispersed aqueous phase. In emulsion technology, the term "dispersed phase" is a term well-known to one skilled in the art which means that the phase exists as small particles or droplets that are suspended in and surrounded by a continuous phase. The dispersed phase is also known as the internal or discontinuous phase. The dispersed aqueous phase is a dispersion of small aqueous particles or droplets suspended in and surrounded by the continuous silicone phase described hereinbefore.

The aqueous phase can be water, or a combination of water and one or more water soluble or dispersible ingredients. Nonlimiting examples of such optional ingredients include thickeners, acids, bases, salts, chelants, gums, water-soluble or dispersible alcohols and polyols, buffers, preservatives, sunscreening agents, colorings, and the like.

The topical compositions of the present invention will typically comprise from about 25% to about 90%, preferably from about 40% to about 80%, more preferably from about 60% to about 80%, water in the dispersed aqueous phase by weight of the composition.

(iii) Emulsifier for Dispersing the Aqueous Phase

The water-in-silicone emulsions of the present invention preferably comprise an emulsifier. In a preferred embodiment, the composition contains from about 0.1% to about 10% emulsifier, more preferably from about 0.5% to about 7.5%, most preferably from about 1% to about 5%, emulsifier by weight of the composition. The emulsifier helps disperse and suspend the aqueous phase within the continuous silicone phase.

A wide variety of emulsifying agents can be employed herein to form the preferred water-in-silicone emulsion. Known or conventional emulsifying agents can be used in the composition, provided that the selected emulsifying agent is chemically and physically compatible with essential components of the composition, and provides the desired dispersion characteristics. Suitable emulsifiers include silicone emulsifiers, non-silicon-containing emulsifiers, and mixtures thereof, known by those skilled in the art for use in topical personal care products. Preferably these emulsifiers have an HLB value of or less than about 14, more preferably from about 2 to about 14, and most preferably from about 4 to about 14. Emulsifiers having an HLB value outside of these ranges can be used in combination with other emulsifiers to achieve an effective weighted average HLB for the combination that falls within these ranges.

Silicone emulsifiers are preferred. A wide variety of silicone emulsifiers are useful herein. These silicone emulsifiers are typically organically modified organopolysiloxanes, also known to those skilled in the art as silicone surfactants. Useful silicone emulsifiers include dimethicone copolyols. These materials are polydimethyl siloxanes which have been modified to include polyether side chains such as polyethylene oxide chains, polypropylene oxide chains, mixtures of these chains, and polyether chains containing moieties derived from both ethylene oxide and propylene oxide. Other examples include alkyl-modified dimethicone copolyols, i.e., compounds which contain C2–C30 pendant side chains. Still other useful dimethicone copolyols include materials having various cationic, anionic, amphoteric, and zwitterionic pendant moieties.

The dimethicone copolyol emulsifiers useful herein can be described by the following general structure:

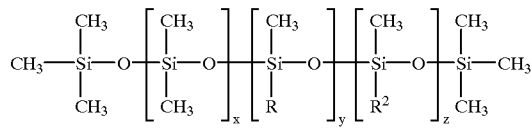

wherein R is C1–C30 straight, branched, or cyclic alkyl and $R^2$ is selected from the group consisting of

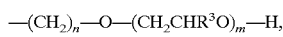

and

wherein n is an integer from 3 to about 10; $R^3$ and $R^4$ are selected from the group consisting of H and C1–C6 straight or branched chain alkyl such that $R^3$ and $R^4$ are not simultaneously the same; and m, o, x, and y are selected such that the molecule has an overall molecular weight from about 200 to about 10,000,000, with m, o, x, and y being independently selected from integers of zero or greater such that m and o are not both simultaneously zero, and z being independently selected from integers of 1 or greater. It is recognized that positional isomers of these copolyols can be achieved. The chemical representations depicted above for the $R^2$ moieties containing the $R^3$ and $R^4$ groups are not meant to be limiting but are shown as such for convenience.

Also useful herein, although not strictly classified as dimethicone copolyols, are silicone surfactants as depicted in the structures in the previous paragraph wherein $R^2$ is:

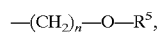

wherein $R^5$ is a cationic, anionic, amphoteric, or zwitterionic moiety.

Nonlimiting examples of dimethicone copolyols and other silicone surfactants useful as emulsifiers herein include polydimethylsiloxane polyether copolymers with pendant polyethylene oxide sidechains, polydimethylsiloxane polyether copolymers with pendant polypropylene oxide sidechains, polydimethylsiloxane polyether copolymers with pendant mixed polyethylene oxide and polypropylene oxide sidechains, polydimethylsiloxane polyether copolymers with pendant mixed poly(ethylene)(propylene)oxide sidechains, polydimethylsiloxane polyether copolymers with pendant organobetaine sidechains, polydimethylsiloxane polyether copolymers with pendant carboxylate sidechains, polydimethylsiloxane polyether copolymers with pendant quaternary ammonium sidechains; and also further modifications of the preceding copolymers containing pendant C2–C30 straight, branched, or cyclic alkyl moieties. Examples of commercially available dimethicone copolyols useful herein sold by Dow Corning Corporation are Dow Corning® 190, 193, Q2-5220, 2501 Wax, 2-5324 fluid, and 3225C (this later material being sold as a mixture with cyclomethicone). Cetyl dimethicone copolyol is commercially available as a mixture with polyglyceryl-4 isostearate (and) hexyl laurate and is sold under the tradename ABIL® WE-09 (available from Goldschmidt). Cetyl dimethicone copolyol is also commercially available as a mixture with hexyl laurate (and) polyglyceryl-3 oleate (and) cetyl dimethicone and is sold under the tradename ABIL® WS-08 (also available from Goldschmidt). Other nonlimiting examples of dimethicone copolyols also include lauryl dimethicone copolyol, dimethicone copolyol acetate, diemethicone copolyol adipate, dimethicone copolyolamine, dimethicone copolyol behenate, dimethicone copolyol butyl ether, dimethicone copolyol hydroxy stearate, dimethicone copolyol isostearate, dimethicone copolyol laurate, dimethicone copolyol methyl ether, dimethicone copolyol phosphate, and dimethicone copolyol stearate. See *International Cosmetic Ingredient Dictionary*, Fifth Edition, 1993.

Dimethicone copolyol emulsifiers useful herein are described, for example, in U.S. Pat. No. 4,960,764, to Figueroa, Jr. et al., issued Oct. 2, 1990; European Patent No. EP 330,369, to SanoGueira, published Aug. 30, 1989; G. H. Dahms, et al., "New Formulation Possibilities Offered by Silicone Copolyols," *Cosmetics & Toiletries*, vol. 110, pp. 91–100, March 1995; M. E. Carlotti et al., "Optimization of W/O-S Emulsions And Study Of The Quantitative Relationships Between Ester Structure And Emulsion Properties," *J. Dispersion Science And Technology*, 13(3), 315–336 (1992);

P. Hameyer, "Comparative Technological Investigations of Organic and Organosilicone Emulsifiers in Cosmetic Water-in-Oil Emulsion Preparations," HAPPI 28(4), pp. 88–128 (1991); J. Smid-Korbar et al., "Efficiency and usability of silicone surfactants in emulsions," *Provisional Communication, International Journal of Cosmetic Science*, 12, 135–139 (1990); and D. G. Krzysik et al., "A New Silicone Emulsifier For Water-in-Oil Systems," *Drug and Cosmetic Industry*, vol. 146(4) pp. 28–81 (April 1990).

Among the non-silicone-containing emulsifiers useful herein are various non-ionic and anionic emulsifying agents such as sugar esters and polyesters, alkoxylated sugar esters and polyesters, C1–C30 fatty acid esters of C1–C30 fatty alcohols, alkoxylated derivatives of C1–C30 fatty acid esters of C1–C30 fatty alcohols, alkoxylated ethers of C1–C30 fatty alcohols, polyglyceryl esters of C1–C30 fatty acids, C1–C30 esters of polyols, C1–C30 ethers of polyols, alkyl phosphates, polyoxyalkylene fatty ether phosphates, fatty acid amides, acyl lactylates, soaps, and mixtures thereof. Other suitable emulsifiers are described, for example, in McCutcheon's, *Detergents and Emulsifiers*, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973.

Nonlimiting examples of these non-silicon-containing emulsifiers include: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, steareth-20, ceteareth-20, PPG-2 methyl glucose ether distearate, ceteth-10, diethanolamine cetyl phosphate, glyceryl stearate, PEG-100 stearate, and mixtures thereof.

b) Oil-in-Water Emulsions

Other preferred topical carriers include oil-in-water emulsions, having a continuous aqueous phase and a hydrophobic, water-insoluble phase ("oil phase") dispersed therein. Examples of suitable carriers comprising oil-in-water emulsions are described in U.S. Pat. No. 5,073,371, to Turner, D. J. et al., issued Dec. 17, 1991, and U.S. Pat. No. 5,073,372, to Turner, D. J. et al., issued Dec. 17, 1991. An especially preferred oil-in-water emulsion, containing a structuring agent, hydrophilic surfactant and water, is described in detail hereinafter.

(i) Structuring Agent

A preferred oil-in-water emulsion comprises a structuring agent to assist in the formation of a liquid crystalline gel network structure. Without being limited by theory, it is believed that the structuring agent assists in providing rheological characteristics to the composition which contribute to the stability of the composition. The structuring agent may also function as an emulsifier or surfactant. Preferred compositions of this invention comprise from about 0.5% to about 20%, more preferably from about 1% to about 10%, most preferably from about 1% to about 5%, by weight of the composition, of a structuring agent.

The preferred structuring agents of the present invention are selected from the group consisting of stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof. More preferred structuring agents of the present invention are selected from the group consisting of stearyl alcohol, cetyl alcohol, behenyl alcohol, the polyethylene glycol ether of stearyl alcohol having an average of about 2 ethylene oxide units (steareth-2), the polyethylene glycol ether of stearyl alcohol having an average of about 21 ethylene oxide units (steareth-21), the polyethylene glycol ether of cetyl alcohol having an average of about 2 ethylene oxide units, and mixtures thereof. Even more preferred structuring agents are selected from the group consisting of stearic acid, palmitic acid, stearyl alcohol, cetyl alcohol, behenyl alcohol, steareth-2, steareth-21, and mixtures thereof.

(ii) Hydrophilic Surfactant

The preferred oil-in-water emulsions comprise from about 0.05% to about 10%, preferably from about 1% to about 6%, and more preferably from about 1% to about 3% of at least one hydrophilic surfactant which can disperse the hydrophobic materials in the water phase (percentages by weight of the topical carrier). The surfactant, at a minimum, must be hydrophilic enough to disperse in water.

Suitable surfactants include any of a wide variety of known cationic, anionic, zwitterionic, and amphoteric surfactants. See, *McCutcheon's, Detergents and Emulsifiers*, North American Edition (1986), published by Allured Publishing Corporation; U.S. Pat. No. 5,011,681; U.S. Pat. No. 4,421,769; and U.S. Pat. No. 3,755,560; these references are incorporated herein by reference in their entirety.

The exact surfactant chosen will depend upon the pH of the composition and the other components present.

Preferred are cationic surfactants, especially dialkyl quaternary ammonium compounds, examples of which are described in U.S. Pat. No. 5,151,209; U.S. Pat. No. 5,151,210; U.S. Pat. No. 5,120,532; U.S. Pat. No. 4,387,090; U.S. Pat. No. 3,155,591; U.S. Pat. No. 3,929,678; U.S. Pat. No. 3,959,461; *McCutcheon's, Detergents & Emulsifiers*, (North American edition 1979) M. C. Publishing Co.; and Schwartz, et al., *Surface Active Agents, Their Chemistry and Technology*, New York: Interscience Publishers, 1949; which descriptions are incorporated herein by reference. The cationic surfactants useful herein include cationic ammonium salts such as those having the formula:

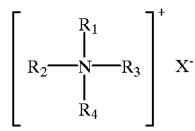

wherein $R_1$, is an alkyl group having from about 12 to about 30 carbon atoms, or an aromatic, aryl or alkaryl group having from about 12 to about 30 carbon atoms; $R_2$, $R_3$, and $R_4$ are independently selected from hydrogen, an alkyl group having from about 1 to about 22 carbon atoms, or aromatic, aryl or alkaryl groups having from about 12 to about 22 carbon atoms; and X is any compatible anion, preferably selected from the group consisting of chloride, bromide, iodide, acetate, phosphate, nitrate, sulfate, methyl sulfate, ethyl sulfate, tosylate, lactate, citrate, glycolate, and mixtures thereof. Additionally, the alkyl groups of $R_1$, $R_2$, $R_3$, and $R_4$ can also contain ester and/or ether linkages, or hydroxy or amino group substituents (e.g., the alkyl groups can contain polyethylene glycol and polypropylene glycol moieties).

More preferably, $R_1$ is an alkyl group having from about 12 to about 22 carbon atoms; $R_2$ is selected from H or an alkyl group having from about 1 to about 22 carbon atoms; $R_3$ and $R_4$ are independently selected from H or an alkyl group having from about 1 to about 3 carbon atoms; and X is as described previously.

Most preferably, $R_1$ is an alkyl group having from about 12 to about 22 carbon atoms; $R_2$, $R_3$, and $R_4$ are selected from H or an alkyl group having from about 1 to about 3 carbon atoms; and X is as described previously.

Alternatively, other useful cationic emulsifiers include amino-amides, wherein in the above structure $R_1$ is alternatively $R_5CONH—(CH_2)_n$, wherein $R_5$ is an alkyl group having from about 12 to about 22 carbon atoms, and n is an integer from about 2 to about 6, more preferably from about 2 to about 4, and most preferably from about 2 to about 3. Nonlimiting examples of these cationic emulsifiers include stearamidopropyl PG-dimonium chloride phosphate, behenamidopropyl PG dimonium chloride, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof. Especially preferred is behenamidopropyl PG dimonium chloride.

Nonlimiting examples of quaternary ammonium salt cationic surfactants include those selected from the group consisting of cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl methyl ammonium bromide, and mixtures thereof. Additional quaternary ammonium salts include those wherein the $C_{12}$ to $C_{30}$ alkyl carbon chain is derived from a tallow fatty acid or from a coconut fatty acid. The term "tallow" refers to an alkyl group derived from tallow fatty acids (usually hydrogenated tallow fatty acids), which generally have mixtures of alkyl chains in the $C_{16}$ to $C_{18}$ range. The term "coconut" refers to an alkyl group derived from a coconut fatty acid, which generally have mixtures of alkyl chains in the $C_{12}$ to $C_{14}$ range. Examples of quaternary ammonium salts derived from these tallow and coconut sources include ditallow dimethyl ammonium chloride, ditallow dimethyl ammonium methyl sulfate, di(hydrogenated tallow) dimethyl ammonium chloride, di(hydrogenated tallow) dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, tallow ammonium chloride, coconut ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof. An example of a quaternary ammonium compound having an alkyl group with an ester linkage is ditallowyl oxyethyl dimethyl ammonium chloride.

More preferred cationic surfactants are those selected from the group consisting of behenamidopropyl PG dimonium chloride, dilauryl dimethyl ammonium chloride, distearyl dimethyl ammonium chloride, dimyristyl dimethyl ammonium chloride, dipalmityl dimethyl ammonium chloride, distearyl dimethyl ammonium chloride, stearamidopropyl PG-dimonium chloride phosphate, stearamidopropyl ethyldiammonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Most preferred cationic surfactants are those selected from the group consisting of behenamidopropyl PG dimonium chloride, dilauryl dimethyl ammonium chloride, distearyl dimethyl ammonium chloride, dimyristyl dimethyl ammonium chloride, dipalmityl dimethyl ammonium chloride, and mixtures thereof.

A preferred combination of cationic surfactant and structuring agent is behenamidopropyl PG dimonium chloride and/or behenyl alcohol, wherein the ratio is preferably optimized to maintained to enhance physical and chemical stability, especially when such a combination contains ionic and/or highly polar solvents. This combination is especially useful for delivery of sunscreening agents such as zinc oxide and octyl methoxycinnamate.

A wide variety of anionic surfactants are also useful herein. See, e.g., U.S. Pat. No. 3,929,678, to Laughlin et al., issued Dec. 30, 1975, which is incorporated herein by reference in its entirety. Nonlimiting examples of anionic surfactants include the alkoyl isethionates, and the alkyl and alkyl ether sulfates. The alkoyl isethionates typically have the formula $RCO—OCH_2CH_2SO_3M$ wherein R is alkyl or alkenyl of from about 10 to about 30 carbon atoms, and M is a water-soluble cation such as ammonium, sodium, potassium and triethanolamine. Nonlimiting examples of these isethionates include those alkoyl isethionates selected from the group consisting of ammonium cocoyl isethionate, sodium cocoyl isethionate, sodium lauroyl isethionate, sodium stearoyl isethionate, and mixtures thereof.

The alkyl and alkyl ether sulfates typically have the respective formulae $ROSO_3M$ and $RO(C_2H_4O)_xSO_3M$, wherein R is alkyl or alkenyl of from about 10 to about 30 carbon atoms, x is from about 1 to about 10, and M is a water-soluble cation such as ammonium, sodium, potassium and triethanolamine. Another suitable class of anionic surfactants are the water-soluble salts of the organic, sulfuric acid reaction products of the general formula:

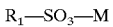

$R_1—SO_3—M$ wherein $R_1$ is chosen from the group consisting of a straight or branched chain, saturated aliphatic hydrocarbon radical having from about 8 to about 24, preferably about 10 to about 16, carbon atoms; and M is a cation. Still other anionic synthetic surfactants include the class designated as succinamates, olefin sulfonates having about 12 to about 24 carbon atoms, and β-alkyloxy alkane sulfonates. Examples of these materials are sodium lauryl sulfate and ammonium lauryl sulfate.

Other anionic materials useful herein are soaps (i.e. alkali metal salts, e.g., sodium or potassium salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.) The fatty acids can also be synthetically prepared. Soaps are described in more detail in U.S. Pat. No. 4,557,853.

Amphoteric and zwitterionic surfactants are also useful herein. Examples of amphoteric and zwitterionic surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 22 carbon atoms (preferably $C_8$–$C_{18}$) and one contains an anionic water solubilizing group, e.g., carboxy, sulfonate, sulfate, phosphate, or phosphonate. Examples are alkyl imino acetates, and iminodialkanoates and aminoalkanoates of the formulas $RN[CH_2)_m CO_2 M]_2$ and $RNH(CH_2)_m CO_2 M$ wherein m is from 1 to 4, R is a $C_8$–$C_{22}$ alkyl or alkenyl, and M is H, alkali metal, alkaline earth metal ammonium, or alkanolammonium. Also included are imidazolinium and ammonium derivatives. Specific examples of suitable amphoteric surfactants include sodium 3-dodecyl-aminopropionate, sodium 3-dodecylaminopropane sulfonate, N-alkyltaurines such as the one prepared by reacting dodecylamine with sodium isethionate according to the teaching of U.S. Pat. No. 2,658,072 which is incorporated herein by reference in its entirety; N-higher alkyl aspartic acids such as those produced according to the teaching of U.S. Pat. No. 2,438,091 which is incorporated herein by reference in its entirety; and the products sold under the trade name "Miranol" and described in U.S. Pat. No. 2,528,378, which is incorporated herein by reference in its entirety. Other examples of useful amphoterics include phosphates, such as coamidopropyl PG-dimonium chloride phosphate (commercially available as Monaquat PTC, from Mona Corp.).

Also useful herein as amphoteric or zwitterionic surfactants are the betaines. Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonzaine 16SP from Lonza Corp.), lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, coco dimethyl sulfopropyl betaine, stearyl dimethyl sulfopropyl betaine, lauryl dimethyl sulfoethyl betaine, lauryl bis-(2-hydroxyethyl) sulfopropyl betaine, and amidobetaines and amidosulfobetaines (wherein the $RCONH(CH_2)_3$ radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Other useful amphoteric and zwitterionic surfactants include the sultaines and hydroxysultaines such as cocamidopropyl hydroxysultaine (available as Mirataine CBS from Rhone-Poulenc), and the alkanoyl sarcosinates corresponding to the formula $RCON(CH_3)CH_2CH_2CO_2M$ wherein R is alkyl or alkenyl of about 10 to about 20 carbon atoms, and M is a water-soluble cation such as ammonium, sodium, potassium and trialkanolamine (e.g., triethanolamine), a preferred example of which is sodium lauroyl sarcosinate.

(iii) Water

The preferred oil-in-water emulsion comprises from about 25% to about 98%, preferably from about 65% to about 95%, more preferably from about 70% to about 90% water by weight of the topical carrier.

The hydrophobic phase is dispersed in the continuous aqueous phase. The hydrophobic phase may contain water insoluble or partially soluble materials such as are known in the art, including but not limited to the silicones described herein in reference to silicone-in-water emulsions, and other oils and lipids such as described above in reference to emulsions.

The topical compositions of the subject invention, including but not limited to lotions and creams, may comprise a dermatologically acceptable emollient. Such compositions preferably contain from about 2% to about 50% of the emollient. As used herein, "emollient" refers to a material useful for the prevention or relief of dryness, as well as for the protection of the skin. A wide variety of suitable emollients are known and may be used herein. Sagarin, *Cosmetics, Science and Technology,* 2nd Edition, Vol. 1, pp. 32–43 (1972), incorporated herein by reference, contains numerous examples of materials suitable as an emollient. A preferred emollient is glycerin. Glycerin is preferably used in an amount of from or about 0.001 to or about 20%, more preferably from or about 0.01 to or about 10%, most preferably from or about 0.1 to or about 5%, e.g., 3%.

Lotions and creams according to the present invention generally comprise a solution carrier system and one or more emollients. Lotions typically comprise from about 1% to about 20%, preferably from about 5% to about 10%, of emollient; from about 50% to about 90%, preferably from about 60% to about 80%, water; and farnesol in the above described amounts. A cream typically comprises from about 5% to about 50%, preferably from about 10% to about 20%, of emollient; from about 45% to about 85%, preferably from about 50% to about 75%, water; and the farnesol in the above described amounts.

Ointments of the present invention may comprise a simple carrier base of animal or vegetable oils or semi-solid hydrocarbons (oleaginous); absorption ointment bases which absorb water to form emulsions; or water soluble carriers, e.g., a water soluble solution carrier. Ointments may further comprise a thickening agent, such as described in Sagarin, *Cosmetics, Science and Technology* 2nd Edition, Vol. 1, pp. 72–73 (1972), incorporated herein by reference, and/or an emollient. For example, an ointment may comprise from about 2% to about 10% of an emollient; from about 0.1% to about 2% of a thickening agent; and farnesol in the above described amount.

Compositions of this invention useful for cleansing ("cleansers") are formulated with a suitable carrier, e.g., as described above, and preferably contain, in addition to farnesol in the above described amounts, from about 1% to about 90%, more preferably from about 5% to about 10%, of a dermatologically acceptable surfactant. The surfactant is suitably selected from anionic, nonionic, zwitterionic, amphoteric and ampholytic surfactants, as well as mixtures of these surfactants. Such surfactants are well known to those skilled in the detergency art. Nonlimiting examples of possible surfactants include isoceteth-20, sodium methyl cocoyl taurate, sodium methyl oleoyl taurate, and sodium lauryl sulfate. See U.S. Pat. No. 4,800,197, to Kowcz et al., issued Jan. 24, 1989, which is incorporated herein by reference in its entirety, for exemplary surfactants useful herein. Examples of a broad variety of additional surfactants useful herein are described in *McCutcheon's Detergents and Emulsifiers*, North American Edition (1986), published by Allured Publishing Corporation. The cleansing compositions can optionally contain, at their art-established levels, other materials which are conventionally used in cleansing compositions.

The physical form of the cleansing compositions is not critical. The compositions can be, for example, formulated as toilet bars, liquids, shampoos, bath gels, hair conditioners, hair tonics, pastes, or mousses. Toilet bars are most preferred since this is the form of cleansing agent most commonly used to wash the skin. Rinse-off cleansing compositions, such as shampoos, require a delivery system adequate to deposit sufficient levels of actives on the skin and scalp. A preferred delivery system involves the use of insoluble complexes. For a more complete disclosure of such delivery systems, see U.S. Pat. No. 4,835,148, Barford et al., issued May 30, 1989.

As used herein, the term "foundation" refers to a liquid, semi-liquid, semi-solid, or solid skin cosmetic which includes, but is not limited to lotions, creams, gels, pastes, cakes, and the like. Typically the foundation is used over a large area of the skin, such as over the face, to provide a particular look. Foundations are typically used to provide an adherent base for color cosmetics such as rouge, blusher, powder and the like, and tend to hide skin imperfections and impart a smooth, even appearance to the skin. Foundations of the present invention include a dermatologically acceptable carrier for the farnesol and may include conventional ingredients such as oils, colorants, pigments, emollients, fragrances, waxes, stabilizers, and the like. Exemplary carriers and such other ingredients which are suitable for use herein are described, for example, in copending patent application Ser. No. 08/430,961, filed on Apr. 28, 1995 in the names of Marcia L. Canter, Brain D. Barford, and Brian D. Hofrichter, and U.K. Patent Application GB 2274585-A, published on Jan. 23, 1993.

Optional Components

The compositions of the present invention may contain a variety of other ingredients such as are conventionally used in a given product type provided that they do not unacceptably alter the benefits of the invention.

In a preferred embodiment, where the composition is to be in contact with human keratinous tissue, the optional components should be suitable for application to keratinous tissue, that is, when incorporated into the composition they are suitable for use in contact with human keratinous tissue without undue toxicity, incompatibility, instability, allergic response, and the like within the scope of sound medical judgment. The *CTFA Cosmetic Ingredient Handbook*, Second Edition (1992) describes a wide variety of nonlimiting cosmetic and pharmaceutical ingredients commonly used in the skin care industry, which are suitable for use in the compositions of the present invention. Examples of these ingredient classes include: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin bleaching and lightening agents (e.g., hydroquinone, kojic acid, ascorbic acid, magnesium ascorbyl phosphate, ascorbyl glucosamine), skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyrrhizinate), skin treating agents, thickeners, and vitamins and derivatives thereof.

In any embodiment of the present invention, however, the actives useful herein can be categorized by the benefit they provide or by their postulated mode of action. However, it is to be understood that the actives useful herein can in some instances provide more than one benefit or operate via more than one mode of action. Therefore, classifications herein are made for the sake of convenience and are not intended to limit the active to that particular application or applications listed.

Desquamation Actives

A safe and effective amount of a desquamation active may be added to the compositions of the present invention, more preferably from about 0.1% to about 10%, even more preferably from about 0.2% to about 5%, also preferably from about 0.5% to about 4%, by weight of the composition. Desquamation actives enhance the skin appearance benefits of the present invention. For example, the desquamation actives tend to improve the texture of the skin (e.g., smoothness). One desquamation system that is suitable for use herein comprises sulfhydryl compounds and zwitterionic surfactants and is described in copending application Ser. No. 08/480,632, filed on Jun. 7, 1995 in the name of Donald L. Bissett, corresponding to PCT Application No. U.S. 95/08136, filed Jun. 29, 1995. Another desquamation system that is suitable for use herein comprises salicylic acid and zwitterionic surfactants and is described in copending patent application Ser. No. 08/554,944, filed on Nov. 13, 1995 as a continuation of Ser. No. 08/209,401, filed on Mar. 9, 1994 in the name of Bissett, corresponding to PCT Application No. 94/12745, filed Nov. 4, 1994, published May 18, 1995. Zwitterionic surfactants such as described in these applications are also useful as desquamatory agents herein, with cetyl betaine being particularly preferred.

Anti-Acne Actives

The compositions of the present invention may comprise a safe and effective amount of one or more anti-acne actives. Examples of useful anti-acne actives include resorcinol, sulfur, salicylic acid, erythromycin, zinc, etc. Further examples of suitable anti-acne actives are described in further detail in U.S. Pat. No. 5,607,980, issued to McAtee et al, on Mar. 4, 1997.

Anti-Wrinkle Actives/Anti-Atrophy Actives

The compositions of the present invention may further comprise a safe and effective amount of one or more anti-wrinkle actives or anti-atrophy actives. Exemplary anti-wrinkle/anti-atrophy actives suitable for use in the compositions of the present invention include sulfur-containing D and L amino acids and their derivatives and salts, particularly the N-acetyl derivatives, a preferred example of which is N-acetyl-L-cysteine; thiols, e.g. ethane thiol; hydroxy acids (e.g., alpha-hydroxy acids such as lactic acid and glycolic acid or beta-hydroxy acids such as salicylic acid and salicylic acid derivatives such as the octanoyl derivative), phytic acid, lipoic acid; lysophosphatidic acid, skin peel agents (e.g., phenol and the like), vitamin $B_3$ compounds and retinoids which enhance the keratinous tissue appearance benefits of the present invention, especially in regulating keratinous tissue condition, e.g., skin condition.

a) Vitamin $B_3$ Compounds

The compositions of the present invention may comprise a safe and effective amount of a vitamin $B_3$ compound.

Vitamin $B_3$ compounds are particularly useful for regulating skin condition as described in co-pending U.S. application Ser. No. 08/834,010, filed Apr. 11, 1997 (corresponding to international publication WO 97/39733 A1, published Oct. 30, 1997). When vitamin $B_3$ compounds are present in the compositions of the instant invention, the compositions preferably comprise from about 0.01% to about 50%, more preferably from about 0.1% to about 10%, even more preferably from about 0.5% to about 10%, and still more preferably from about 1% to about 5%, most preferably from about 2% to about 5%, by weight of the composition, of the vitamin $B_3$ compound.

As used herein, "vitamin $B_3$ compound" means a compound having the formula:

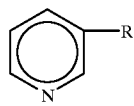

wherein R is —$CONH_2$ (i.e., niacinamide), —COOH (i.e., nicotinic acid) or —$CH_2OH$ (i.e., nicotinyl alcohol); derivatives thereof; and salts of any of the foregoing.

Exemplary derivatives of the foregoing vitamin $B_3$ compounds include nicotinic acid esters, including non-vasodilating esters of nicotinic acid (e.g., tocopheryl nicotinate), nicotinyl amino acids, nicotinyl alcohol esters of carboxylic acids, nicotinic acid N-oxide and niacinamide N-oxide.

Examples of suitable vitamin $B_3$ compounds are well known in the art and are commercially available from a number of sources, e.g., the Sigma Chemical Company (St. Louis, Mo.); ICN Biomedicals, Inc. (Irvin, Calif.) and Aldrich Chemical Company (Milwaukee, Wis.).

The vitamin compounds may be included as the substantially pure material, or as an extract obtained by suitable physical and/or chemical isolation from natural (e.g., plant) sources.

b) Retinoids

The compositions of the present invention may also comprise a retinoid. As used herein, "retinoid" includes all natural and/or synthetic analogs of Vitamin A or retinol-like compounds which possess the biological activity of Vitamin A in the skin as well as the geometric isomers and stereoisomers of these compounds. The retinoid is preferably retinol, retinol esters (e.g., $C_2$–$C_{22}$ alkyl esters of retinol, including retinyl palmitate, retinyl acetate, retinyl propionate), retinal, and/or retinoic acid (including all-trans retinoic acid and/or 13-cis-retinoic acid), more preferably retinoids other than retinoic acid. These compounds are well known in the art and are commercially available from a number of sources, e.g., Sigma Chemical Company (St. Louis, Mo.), and Boerhinger Mannheim (Indianapolis, Ind.). Other retinoids which are useful herein are described in U.S. Pat. Nos. 4,677,120, issued Jun. 30, 1987 to Parish et al.; 4,885,311, issued Dec. 5, 1989 to Parish et al.; 5,049,584, issued Sep. 17, 1991 to Purcell et al.; 5,124,356, issued Jun. 23, 1992 to Purcell et al.; and Reissue 34,075, issued Sep. 22, 1992 to Purcell et al. Other suitable retinoids are tocopheryl-retinoate [tocopherol ester of retinoic acid (trans- or cis-), adapalene {6-[3-(1-adamantyl)-4-methoxyphenyl]-2-naphthoic acid}, and tazarotene (ethyl 6-[2-(4,4-dimethylthiochroman-6-yl)ethynyl]nicotinate). Preferred retinoids are retinol, retinyl palmitate, retinyl acetate, retinyl propionate, retinal and combinations thereof.

The retinoid may be included as the substantially pure material, or as an extract obtained by suitable physical and/or chemical isolation from natural (e.g., plant) sources. The retinoid is preferably substantially pure, more preferably essentially pure.

The compositions of this invention may contain a safe and effective amount of the retinoid, such that the resultant composition is safe and effective for regulating keratinous tissue condition, preferably for regulating visible and/or tactile discontinuities in skin, more preferably for regulating signs of skin aging, even more preferably for regulating visible and/or tactile discontinuities in skin texture associated with skin aging. The compositions preferably contain from or about 0.005% to or about 2%, more preferably 0.01% to or about 2%, retinoid. Retinol is most preferably used in an amount of from or about 0.01% to or about 0.15%; retinol esters are most preferably used in an amount of from or about 0.01% to or about 2% (e.g., about 1%); retinoic acids are most preferably used in an amount of from or about 0.01% to or about 0.25%; tocopheryl-retinoate, adapalene, and tazarotene are most preferably used in an amount of from or about 0.01 % to or about 2%.

Where the compositions of the present invention contain both a retinoid and a Vitamin $B_3$ compound, the retinoid is preferably used in the above amounts, and the vitamin $B_3$ compound is preferably used in an amount of from or about 0.1% to or about 10%, more preferably from or about 2% to or about 5%.

Peptides

Peptides, including but not limited to, di-, tri-, tetra-, and pentapeptides and derivatives thereof, may be included in the compositions of the present invention in amounts that are safe and effective. Suitable peptides include dipeptides like Carnosine (beta-ala-his), tripeptides like Biopeptide CL® (palmitoyl-gly-his-lys) (commercially available from Sederma, France), tribasic tripeptides and tetrapeptides, including but not limited to Peptide E (Arg-Ser-Arg-Lys) (SEQ ID NO:1), Peptide CK (Arg-Lys-Arg), Peptide CK+ (Ac-Arg-Lys-Arg-$NH_2$); the peptides His-Gly-Gly and Iamin, and combinations thereof. Pentapeptides or pentapeptide derivatives like Matrixyl® (palmitoyl-lys-thr-thr-lys-ser) (SEQ ID NO:2) (commercially available from Sederma, France) are also suitable for inclusion in compositions of the present invention.

Preferably, the peptide is selected from the group consisting of palmitoyl-lys-thr-thr-lys-ser, palmitoyl-gly-his-lys, beta-ala-his, Arg-Ser-Arg-Lys, Arg-Lys-Arg, Ac-Arg-Lys-Arg-$NH_2$, His-Gly-Gly, Iamin, their derivatives, and combinations thereof. More preferably, the peptide is selected from the group consisting of palmitoyl-lys-thr-thr-lys-ser, palmitoyl-gly-his-lys, beta-ala-his, their derivatives, and combinations thereof. Even more preferably, the peptide is selected from the group consisting of palmitoyl-lys-thr-thr-lys-ser, palmitoyl-gly-his-lys, their derivatives, and combinations thereof. Most preferably, the peptide is selected from the group consisting of palmitoyl-lys-thr-thr-lys-ser and derivatives thereof.

When included in the present compositions, peptides are preferably included in amounts of from about $1\times10^{31}$ $^6$% to about 10%, by weight of the composition. In certain compositions where the peptide is Carnosine®, the compositions preferably comprise from about 0.1% to about 5%, by weight of the composition, of such peptides. In other embodiments where Matrixyl® is included, the compositions preferably comprise from about 0.0001% to about 0.01%, by weight of the composition, of Matrixyl®. Other peptides and their derivatives are preferably included in the compositions of the present invention in amounts of from about 0.00001% to about 0.01%.

Anti-Oxidants/Radical Scavengers

The compositions of the present invention may include a safe and effective amount of an anti-oxidant/radical scavenger. The anti-oxidant/radical scavenger is especially useful for providing protection against UV radiation which can cause increased scaling or texture changes in the stratum corneum and against other environmental agents which can cause skin damage.

A safe and effective amount of an anti-oxidant/radical scavenger may be added to the compositions of the subject invention, preferably from about 0.1% to about 10%, more preferably from about 1% to about 5%, of the composition.

Anti-oxidants/radical scavengers such as ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts may be used. Preferred anti-oxidants/radical scavengers are selected from tocopherol sorbate and other esters of tocopherol, more preferably tocopherol sorbate. For example, the use of tocopherol sorbate in topical compositions and applicable to the present invention is described in U.S. Pat. No. 4,847,071, issued on Jul. 11, 1989 to Donald L. Bissett, Rodney D. Bush and Ranjit Chatterjee.

Chelators

The compositions of the present invention may also comprise a safe and effective amount of a chelator or chelating agent. As used herein, "chelator" or "chelating agent" means an active agent capable of removing a metal ion from a system by forming a complex so that the metal ion cannot readily participate in or catalyze chemical reactions. The inclusion of a chelating agent is especially useful for providing protection against UV radiation which can contribute to excessive scaling or skin texture changes and against other environmental agents which can cause skin damage.

A safe and effective amount of a chelating agent may be added to the compositions of the subject invention, preferably from about 0.1% to about 10%, more preferably from about 1% to about 5%, of the composition. Exemplary chelators that are useful herein are disclosed in U.S. Pat. No. 5,487,884, issued Jan. 30, 1996 to Bissett et al.; International Publication No. 91/16035, Bush et al., published Oct. 31, 1995; and International Publication No. 91/16034, Bush et al., published Oct. 31, 1995. Preferred chelators useful in compositions of the subject invention are furildioxime, furilmonoxime, and derivatives thereof.

Flavonoids

The compositions of the present invention may optionally comprise a flavonoid compound. Flavonoids are broadly disclosed in U.S. Pat. Nos. 5,686,082 and 5,686,367, both of which are herein incorporated by reference. Flavonoids suitable for use in the present invention are flavanones selected from the group consisting of unsubstituted flavanones, mono-substituted flavanones, and mixtures thereof; chalcones selected from the group consisting of unsubstituted chalcones, mono-substituted chalcones, di-substituted chalcones, tri-substituted chalcones, and mixtures thereof; flavones selected from the group consisting of unsubstituted flavones, mono-substituted flavanones, di-substituted flavones, and mixtures thereof; one or more isoflavones; coumarins selected from the group consisting of unsubstituted coumarins, mono-substituted coumarins, di-substituted coumarins, and mixtures thereof; chromones selected from the group consisting of unsubstituted chromones, mono-substituted chromones, di-substituted chromones, and mixtures thereof; one or more dicoumarols; one or more chromanones; one or more chromanols; isomers (e.g., cis/trans isomers) thereof; and mixtures thereof. By the term "substituted" as used herein means flavonoids wherein one or more hydrogen atom of the flavonoid has been independently replaced with hydroxyl, C1–C8 alkyl, C1–C4 alkoxyl, O-glycoside, and the like or a mixture of these substituents.

Examples of suitable flavonoids include, but are not limited to, unsubstituted flavanone, mono-hydroxy flavanones (e.g., 2'-hydroxy flavanone, 6-hydroxy flavanone, 7-hydroxy flavanone, etc.), mono-alkoxy flavanones (e.g., 5-methoxy flavanone, 6-methoxy flavanone, 7-methoxy flavanone, 4'-methoxy flavanone, etc.), unsubstituted chalcone (especially unsubstituted trans-chalcone), mono-hydroxy chalcones (e.g., 2'-hydroxy chalcone, 4'-hydroxy chalcone, etc.), di-hydroxy chalcones (e.g., 2',4-dihydroxy chalcone, 2',4'-dihydroxy chalcone, 2,2'-dihydroxy chalcone, 2',3-dihydroxy chalcone, 2',5'-dihydroxy chalcone, etc.), and tri-hydroxy chalcones (e.g., 2',3',4'-trihydroxy chalcone, 4,2',4'-trihydroxy chalcone, 2,2',4'-trihydroxy chalcone, etc.), unsubstituted flavone, 7,2'-dihydroxy flavone, 3',4'-dihydroxy naphthoflavone, 4'-hydroxy flavone, 5,6-benzoflavone, and 7,8-benzoflavone, unsubstituted isoflavone, daidzein (7,4'-dihydroxy isoflavone), 5,7-dihydroxy-4'-methoxy isoflavone, soy isoflavones (a mixture extracted from soy), unsubstituted coumarin, 4-hydroxy coumarin, 7-hydroxy coumarin, 6-hydroxy-4-methyl coumarin, unsubstituted chromone, 3-formyl chromone, 3-formyl-6-isopropyl chromone, unsubstituted dicoumarol, unsubstituted chromanone, unsubstituted chromanol, and mixtures thereof.

Preferred for use herein are unsubstituted flavanone, methoxy flavanones, unsubstituted chalcone, 2',4-dihydroxy chalcone, and mixtures thereof. Most preferred are unsubstituted flavanone, unsubstituted chalcone (especially the trans isomer), and mixtures thereof.

They can be synthetic materials or obtained as extracts from natural sources (e.g., plants). The naturally sourced material can also further be derivatized (e.g., an ester or ether derivative prepared following extraction from a natural source). Flavonoid compounds useful herein are commercially available from a number of sources, e.g., Indofine Chemical Company, Inc. (Somerville, N.J.), Steraloids, Inc. (Wilton, N.H.), and Aldrich Chemical Company, Inc. (Milwaukee, Wis.).

Mixtures of the above flavonoid compounds may also be used.

The herein described flavonoid compounds are preferably present in the instant invention at concentrations of from about 0.01% to about 20%, more preferably from about 0.1% to about 10%, and most preferably from about 0.5% to about 5%.

Anti-Inflammatory Agents

A safe and effective amount of an anti-inflammatory agent may be added to the compositions of the present invention, preferably from about 0.1% to about 10%, more preferably from about 0.5% to about 5%, of the composition. The anti-inflammatory agent enhances the skin appearance benefits of the present invention, e.g., such agents contribute to a more uniform and acceptable skin tone or color. The exact amount of anti-inflammatory agent to be used in the compositions will depend on the particular anti-inflammatory agent utilized since such agents vary widely in potency.

Steroidal anti-inflammatory agents, including but not limited to, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. The preferred steroidal anti-inflammatory for use is hydrocortisone.

A second class of anti-inflammatory agents which is useful in the compositions includes the nonsteroidal anti-inflammatory agents. The variety of compounds encompassed by this group are well-known to those skilled in the art. For detailed disclosure of the chemical structure, synthesis, side effects, etc. of non-steroidal anti-inflammatory agents, one may refer to standard texts, including *Anti-inflammatory and Anti-Rheumatic Drugs*, K. D. Rainsford, Vol. I–III, CRC Press, Boca Raton, (1985), and *Anti-inflammatory Agents, Chemistry and Pharmacology*, 1, R. A. Scherrer, et al., Academic Press, New York (1974).

Specific non-steroidal anti-inflammatory agents useful in the composition invention include, but are not limited to:

1) the oxicams, such as piroxicam, isoxicam, tenoxicam, sudoxicam, and CP-14,304;
2) the salicylates, such as aspirin, disalcid, benorylate, trilisate, safapryn, solprin, diflunisal, and fendosal;
3) the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac;
4) the fenamates, such as mefenamic, meclofenamic, flufenamic, niflumic, and tolfenamic acids;
5) the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and
6) the pyrazoles, such as phenylbutazone, oxyphenbutazone, feprazone, azapropazone, and trimethazone.

Mixtures of these non-steroidal anti-inflammatory agents may also be employed, as well as the dermatologically acceptable salts and esters of these agents. For example, etofenamate, a flufenamic acid derivative, is particularly useful for topical application. Of the nonsteroidal anti-inflammatory agents, ibuprofen, naproxen, flufenamic acid, etofenamate, aspirin, mefenamic acid, meclofenamic acid, piroxicam and felbinac are preferred; ibuprofen, naproxen, ketoprofen, etofenamate, aspirin and flufenamic acid are most preferred.

Finally, so-called "natural" anti-inflammatory agents are useful in methods of the present invention. Such agents may suitably be obtained as an extract by suitable physical and/or chemical isolation from natural sources (e.g., plants, fungi, by-products of microorganisms) or can be synthetically prepared. For example, candelilla wax, bisabolol (e.g., alpha bisabolol), aloe vera, plant sterols (e.g., phytosterol), Manjistha (extracted from plants in the genus Rubia, particularly *Rubia cordifolia*), and Guggal (extracted from plants in the genus Commiphora, particularly *Commiphora mukul*), kola extract, chamomile, red clover extract, and sea whip extract, may be used.

Additional anti-inflammatory agents useful herein include compounds of the Licorice (the plant genus/species *Glycyrrhiza glabra*) family, including glycyrrhetic acid, glycyrrhizic acid, and derivatives thereof (e.g., salts and esters). Suitable salts of the foregoing compounds include metal and ammonium salts. Suitable esters include $C_2$–$C_{24}$ saturated or unsaturated esters of the acids, preferably $C_{10}$–$C_{24}$, more preferably $C_{16}$–$C_{24}$. Specific examples of the foregoing include oil soluble licorice extract, the glycyrrhizic and glycyrrhetic acids themselves, monoammonium glycyrrhizinate, monopotassium glycyrrhizinate, dipotassium glycyrrhizinate, 1-beta-glycyrrhetic acid, stearyl glycyrrhetinate, and 3-stearyloxy-glycyrrhetinic acid, and disodium 3-succinyloxy-beta-glycyrrhetinate. Stearyl glycyrrhetinate is preferred.

Anti-Cellulite Agents

The compositions of the present invention may also comprise a safe and effective amount of an anti-cellulite agent. Suitable agents may include, but are not limited to, xanthine compounds (e.g., caffeine, theophylline, theobromine, and aminophylline).

Topical Anesthetics

The compositions of the present invention may also comprise a safe and effective amount of a topical anesthetic. Examples of topical anesthetic drugs include benzocaine, lidocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof.

Tanning Actives

The compositions of the present invention may comprise a tanning active. When present, it is preferable that the compositions comprise from about 0.1% to about 20%, more preferably from about 2% to about 7%, and most preferably from about 3% to about 6%, by weight of the composition, of dihydroxyacetone as an artificial tanning active.

Dihydroxyacetone, which is also known as DHA or 1,3-dihydroxy-2-propanone, is a white to off-white, crystalline powder. This material can be represented by the chemical formula $C_3H_6O_3$ and the following chemical structure.

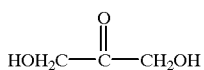

The compound can exist as a mixture of monomers and dimers, with the dimers predominating in the solid crystalline state. Upon heating or melting, the dimers break down to yield the monomers. This conversion of the dimeric form to the monomeric form also occurs in aqueous solution. Dihydroxyacetone is also known to be more stable at acidic pH values. See *The Merck Index*, Tenth Edition, entry 3167, p. 463 (1983), and "Dihydroxyacetone for Cosmetics", E. Merck Technical Bulletin, 03-304110, 319 897, 180 588.

Skin Lightening Agents

The compositions of the present invention may comprise a skin lightening agent. When used, the compositions preferably comprise from about 0.1% to about 10%, more preferably from about 0.2% to about 5%, also preferably from about 0.5% to about 2%, by weight of the composition, of a skin lightening agent. Suitable skin lightening agents include those known in the art, including kojic acid, arbutin, ascorbic acid and derivatives thereof (e.g., magnesium ascorbyl phosphate or sodium ascorbyl phosphate), and extracts (e.g., mulberry extract, placental extract). Skin lightening agents suitable for use herein also include those described in copending patent application Ser. No. 08/479,935, filed on Jun. 7, 1995 in the name of Hillebrand, corresponding to PCT Application No. U.S. 95/07432, filed Jun. 12, 1995; and copending patent application Ser. No. 08/390,152, filed on Feb. 24, 1995 in the names of Kalla L. Kvalnes, Mitchell A. DeLong, Barton J. Bradbury, Curtis B. Motley, and John D. Carter, corresponding to PCT Application No. U.S. 95/02809, filed Mar. 1, 1995, published Sep. 8, 1995.

Antimicrobial and Antifungal Actives

The compositions of the present invention may comprise an antimicrobial or antifungal active. Such actives are capable of destroying microbes, preventing the development of microbes or preventing the pathogenic action of microbes. A safe and effective amount of an antimicrobial or antifungal active may be added to the present compositions, preferably, from about 0.001% to about 10%, more preferably from about 0.01% to about 5%, and most preferably from about 0.05% to about 2%.

Examples of antimicrobial and antifungal actives include β-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, ketaconazole, amanfadine hydrochloride, amanfadine sulfate, octopirox, parachlorometa xylenol, nystatin, tolnaftate, zinc pyrithione and clotrimazole.

Preferred examples of actives useful herein include those selected from the group consisting of salicylic acid, benzoyl peroxide, 3-hydroxy benzoic acid, glycolic acid, lactic acid, 4-hydroxy benzoic acid, acetyl salicylic acid, 2-hydroxybutanoic acid, 2-hydroxypentanoic acid, 2-hydroxyhexanoic acid, cis-retinoic acid, trans-retinoic acid, retinol, phytic acid, N-acetyl-L-cysteine, lipoic acid, azelaic acid, arachidonic acid, benzoylperoxide, tetracycline, ibuprofen, naproxen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, lidocaine hydrochloride, clotrimazole, miconazole, ketoconazole, neocycin sulfate, and mixtures thereof.

Sunscreen Actives

Exposure to ultraviolet light can result in excessive scaling and texture changes of the stratum corneum. Therefore, the compositions of the subject invention may optionally contain a sunscreen active. As used herein, "sunscreen active" includes both sunscreen agents and physical sunblocks. Suitable sunscreen actives may be organic or inorganic.

A wide variety of conventional sunscreen actives are suitable for use herein. Sagarin, et al., at Chapter VIII, pages 189 et seq., of *Cosmetics Science and Technology* (1972), discloses numerous suitable actives. Specific suitable sunscreen actives include, for example: p-aminobenzoic acid, its salts and its derivatives (ethyl, isobutyl, glyceryl esters; p-dimethylaminobenzoic acid); anthranilates (i.e., o-aminobenzoates; methyl, menthyl, phenyl, benzyl, phenylethyl, linalyl, terpinyl, and cyclohexenyl esters); salicylates (amyl, phenyl, octyl, benzyl, menthyl, glyceryl, and di-propyleneglycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylacetoumbelliferone); trihydroxy-cinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); di-hydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and violuric acids; tannic acid and its derivatives (e.g., hexaethylether); (butyl carbotol) (6-propyl piperonyl) ether; hydroquinone; benzophenones (oxybenzene, sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; butylmethoxydibenzoylmethane; etocrylene; octocrylene; [3-(4'-methylbenzylidene bornan-2-one) and 4-isopropyl-di-benzoylmethane.

Of these, 2-ethylhexyl-p-methoxycinnamate (commercially available as PARSOL MCX), 4,4'-t-butyl methoxydibenzoyl-methane (commercially available as PARSOL 1789), 2-hydroxy-4-methoxybenzophenone, octyldimethyl-p-amninobenzoic acid, digalloyltrioleate, 2,2-dihydroxy-4-methoxybenzophenone, ethyl-4-(bis(hydroxy-propyl))aminobenzoate, 2-ethylhexyl-2-cyano-3, 3-diphenylacrylate, 2-ethylhexyl-salicylate, glyceryl-p-aminobenzoate, 3,3,5-trimethylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene and mixtures of these compounds, are preferred.

More preferred organic sunscreen actives useful in the compositions useful in the subject invention are 2-ethylhexyl-p-methoxycinnamate, butylmethoxydibenzoyl-methane, 2-hydroxy-4-methoxybenzo-phenone, 2-phenylbenzimidazole-5-sulfonic acid, octyldimethyl-p-aminobenzoic acid, octocrylene and mixtures thereof.

Also particularly useful in the compositions are sunscreen actives such as those disclosed in U.S. Pat. No. 4,937,370 issued to Sabatelli on Jun. 26, 1990, and U.S. Pat. No. 4,999,186 issued to Sabatelli & Spirnak on Mar. 12, 1991. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range.

Preferred members of this class of sunscreening agents are 4-N,N-(2-ethylhexyl)methylaminobenzoic acid ester of 2,4-dihydroxybenzophenone; N,N-di-(2-ethylhexyl)-4-aminobenzoic acid ester with 4-hydroxydibenzoylmethane; 4-N,N-(2-ethylhexyl)methyl-aminobenzoic acid ester with 4-hydroxydibenzoylmethane; 4-N,N-(2-ethylhexyl)methyl-aminobenzoic acid ester of 2-hydroxy-4-(2-hydroxyethoxy) benzophenone; 4-N,N-(2-ethylhexyl)-methylaminobenzoic acid ester of 4-(2-hydroxyethoxy)dibenzoylmethane; N,N-di-(2-ethylhexyl)-4-aminobenzoic acid ester of 2-hydroxy-4-(2-hydroxyethoxy)benzophenone; and N,N-di-(2-ethylhexyl)-4-aminobenzoic acid ester of 4-(2-hydroxyethoxy)dibenzoylmethane and mixtures thereof.

Especially preferred sunscreen actives include 4,4'-t-butylmethoxydibenzoylmethane, 2-ethylhexyl-p-methoxycinnamate, phenyl benzimidazole sulfonic acid, and octocrylene.

A safe and effective amount of the sunscreen active is used, typically from about 1% to about 20%, more typically from about 2% to about 10% by weight of the composition. Exact amounts will vary depending upon the sunscreen chosen and the desired Sun Protection Factor (SPF).

Conditioning Agents

The compositions of the present invention may comprise a conditioning agent selected from the group consisting of humectants, moisturizers, or skin conditioners. A variety of these materials can be employed and each can be present at a level of from about 0.01% to about 20%, more preferably from about 0.1% to about 10%, and most preferably from about 0.5% to about 7% by weight of the composition. These materials include, but are not limited to, guanidine; urea; glycolic acid and glycolate salts (e.g. ammonium and quaternary alkyl ammonium); salicylic acid; lactic acid and lactate salts (e.g., ammonium and quaternary alkyl ammonium); aloe vera in any of its variety of forms (e.g., aloe vera gel); polyhydroxy alcohols such as sorbitol, mannitol, xylitol, erythritol, glycerol, hexanetriol, butanetriol, propylene glycol, butylene glycol, hexylene glycol and the like; polyethylene glycols; sugars (e.g., melibiose) and starches; sugar and starch derivatives (e.g., alkoxylated glucose, fucose, glucosamine); hyaluronic acid; lactamide monoethanolamine; acetamide monoethanolamine; panthenol; allantoin; and mixtures thereof. Also useful herein are the propoxylated glycerols described in U.S. Pat. No. 4,976,953, to Orr et al, issued Dec. 11, 1990.

Also useful are various $C_1$–$C_{30}$ monoesters and polyesters of sugars and related materials. These esters are derived from a sugar or polyol moiety and one or more carboxylic acid moieties. Such ester materials are further described in, U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977, U.S. Pat. No. 5,306,516, to Letton et al, issued Apr. 26, 1994; U.S. Pat. No. 5,306,515, to Letton et al, issued Apr. 26, 1994; U.S. Pat. No. 5,305,514, to Letton et al, issued Apr. 26, 1994; U.S. Pat. No. 4,797,300, to Jandacek et al, issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985.

Preferably, the conditioning agent is selected from the group consisting of urea, guanidine, sucrose polyester, panthenol, allantoin, and combinations thereof.

Thickening Agent (Including Thickeners and Gelling Agents)

The compositions of the present invention can comprise one or more thickening agents, preferably from about 0.1% to about 5%, more preferably from about 0.1% to about 3%, and most preferably from about 0.25% to about 2%, by weight of the composition.

Nonlimiting classes of thickening agents include those selected from the group consisting of:

a) Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. Polymers useful in the present invention are more fully described in U.S. Pat. No. 5,087,445, to Haffey et al, issued Feb. 11, 1992; U.S. Pat. No. 4,509,949, to Huang et al, issued Apr. 5, 1985; U.S. Pat. No. 2,798,053, to Brown, issued Jul. 2, 1957; and in CTFA *International Cosmetic Ingredient Dictionary*, Fourth Edition, 1991, pp. 12 and 80.

Examples of commercially available carboxylic acid polymers useful herein include the carbomers, which are homopolymers of acrylic acid crosslinked with allyl ethers of sucrose or pentaerytritol. The carbomers are available as the Carbopol® 900 series from B. F. Goodrich (e.g., Carbopol® 954). In addition, other suitable carboxylic acid polymeric agents include copolymers of $C_{10-30}$ alkyl acrylates with one or more monomers of acrylic acid, methacrylic acid, or one of their short chain (i.e., $C_{1-4}$ alcohol) esters, wherein the crosslinking agent is an allyl ether of sucrose or pentaerytritol. These copolymers are known as acrylates/$C_{10-30}$ alkyl acrylate crosspolymers and are commercially available as Carbopol® 1342, Carbopol® 1382, Pemulen TR-1, and Pemulen TR-2, from B. F. Goodrich. In other words, examples of carboxylic acid polymer thickeners useful herein are those selected from the group consisting of carbomers, acrylates/$C_{10}$–$C_{30}$ alkyl acrylate crosspolymers, and mixtures thereof.

b) Crosslinked Polyacrylate Polymers

The compositions of the present invention can optionally comprise crosslinked polyacrylate polymers useful as thickeners or gelling agents including both cationic and nonionic polymers, with the cationics being generally preferred. Examples of useful crosslinked nonionic polyacrylate polymers and crosslinked cationic polyacrylate polymers are those described in U.S. Pat. No. 5,100,660, to Hawe et al, issued Mar. 31, 1992; U.S. Pat. No. 4,849,484, to Heard, issued Jul. 18, 1989; U.S. Pat. No. 4,835,206, to Farrar et al, issued May 30, 1989; U.S. Pat. No. 4,628,078 to Glover et al issued Dec. 9, 1986; U.S. Pat. No. 4,599,379 to Flesher et al issued Jul. 8, 1986; and EP 228,868, to Farrar et al, published Jul. 15, 1987.

c) Polyacrylamide Polymers

The compositions of the present invention can optionally comprise polyacrylamide polymers, especially nonionic polyacrylamide polymers including substituted branched or unbranched polymers. Most preferred among these polyacrylamide polymers is the nonionic polymer given the CTFA designation polyacrylamide and isoparaffin and laureth-7, available under the Tradename Sepigel 305 from Seppic Corporation (Fairfield, N.J.).

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc., (Patterson, N.J.).

d) Polysaccharides

A wide variety of polysaccharides are useful herein. "Polysaccharides" refer to gelling agents which contain a backbone of repeating sugar (i.e., carbohydrate) units. Nonlimiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl substituted celluloses. In these polymers, the hydroxy groups of the cellulose polymer is hydroxyalkylated (preferably hydroxyethylated or hydroxypropylated) to form a hydroxyalkylated cellulose which is then further modified with a $C_{10}$–$C_{30}$ straight chain or branched chain alkyl group through an ether linkage. Typically these polymers are ethers of $C_{10}$–$C_{30}$ straight or branched chain alcohols with hydroxyalkylcelluloses. Examples of alkyl groups useful herein include those selected from the group consisting of stearyl, isostearyl, lauryl, myristyl, cetyl, isocetyl, cocoyl (i.e. alkyl groups derived from the alcohols of coconut oil), palmityl, oleyl, linoleyl, linolenyl, ricinoleyl, behenyl, and mixtures thereof. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation (Wilmington, Del.).

Other useful polysaccharides include scleroglucans comprising a linear chain of (1–3) linked glucose units with a (1–6) linked glucose every three units, a commercially available example of which is Clearogel® CS11 from Michel Mercier Products Inc. (Mountainside, N.J.).

e) Gums

Other thickening and gelling agents useful herein include materials which are primarily derived from natural sources. Nonlimiting examples of these gelling agent gums include materials selected from the group consisting of acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

Preferred compositions of the present invention include a thickening agent selected from the group consisting of carboxylic acid polymers, crosslinked polyacrylate polymers, polyacrylamide polymers, and mixtures thereof, more preferably selected from the group consisting of carboxylic acid polymers, polyacrylamide polymers, and mixtures thereof.

While a variety of optional components may be included in the compositions of the presently claimed methods, the compositions are preferably free of water-dispersible lecithin and panthenol. As used herein, "free of" means that the compound or component may not be detected in the compositions.

Composition Preparation

The compositions useful for the methods of the present invention are generally prepared by conventional methods such as are known in the art of making topical compositions. Such methods typically involve mixing of the ingredients in one or more steps to a relatively uniform state, with or without heating, cooling, application of vacuum, and the like.

Methods for Regulating Keratinous Tissue Condition

The compositions of the present invention are useful for regulating mammalian keratinous tissue condition. Such regulation of keratinous tissue conditions include prophylactic and therapeutic regulation. More specifically, such regulating methods are directed to thickening keratinous tissue (i.e., building the epidermis and/or dermis layers of the skin and where applicable the keratinous layers of the nail and hair shaft) and preventing and/or retarding atrophy of mammalian skin, preventing and/or retarding the appearance of spider vessels and/or red blotchiness on mammalian skin, preventing and/or retarding the appearance of dark circles under the eye of a mammal, preventing and/or retarding sallowness of mammalian skin, preventing and/or retarding sagging of mammalian skin, softening and/or smoothing lips, hair and nails of a mammal, and preventing and/or relieving itch of mammalian skin.

Regulating keratinous tissue condition involves topically applying to the keratinous tissue a safe and effective amount of a composition of the present invention. The amount of the composition which is applied, the frequency of application and the period of use will vary widely depending upon the level of farnesol and/or other components of a given composition and the level of regulation desired, e.g., in light of the level of keratinous tissue damage present or expected to occur.

In a preferred embodiment, the composition is chronically applied to the skin. By "chronic topical application" is meant continued topical application of the composition over an extended period during the subject's lifetime, preferably for a period of at least about one week, more preferably for a period of at least about one month, even more preferably for at least about three months, even more preferably for at least about six months, and more preferably still for at least about one year. While benefits are obtainable after various maximum periods of use (e.g., five, ten or twenty years), it is preferred that chronic application continue throughout the subject's lifetime. Typically applications would be on the order of about once per day over such extended periods, however application rates can vary from about once per week up to about three times per day or more.

A wide range of quantities of the compositions of the present invention can be employed to provide a skin appearance and/or feel benefit. Quantities of the present compositions which are typically applied per application are, in mg composition/cm² skin, from about 0.1 mg/cm² to about 10 mg/cm². A particularly useful application amount is about 1 mg/cm² to about 2 mg/cm².

Regulating keratinous tissue condition is preferably practiced by applying a composition in the form of a skin lotion, cream, gel, foam, ointment, paste, emulsion, spray, conditioner, tonic, cosmetic, lipstick, foundation, nail polish, after-shave, or the like which is preferably intended to be left on the skin or other keratin structure for some esthetic, prophylactic, therapeutic or other benefit (i.e., a "leave-on" composition). After applying the composition to the skin, it is preferably left on the skin for a period of at least about 15 minutes, more preferably at least about 30 minutes, even more preferably at least about 1 hour, most preferably for at least several hours, e.g., up to about 12 hours. Any part of the external portion of the face, hair, and/or nails can be treated, e.g., face, lips, under-eye area, eyelids, scalp, neck, torso, arms, hands, legs, feet, fingernails, toenails, scalp hair, eyelashes, eyebrows, etc. The composition can be applied with the fingers or with an implement or device (e.g., pad, cotton ball, applicator pen, spray applicator, and the like).

Another approach to ensure a continuous exposure of the skin to at least a minimum level of the farnesol is to apply the compound by use of a patch applied, e.g., to the face. Such an approach is particularly useful for problem skin areas needing more intensive treatment (e.g., facial crows feet area, frown lines, under eye area, and the like). The patch can be occlusive, semi-occlusive or non-occlusive and can be adhesive or non-adhesive. The farnesol composition can be contained within the patch or be applied to the skin prior to application of the patch. The patch can also include additional actives such as chemical initiators for exothermic reactions such as those described in PCT application WO 9701313 to Burkett et al. The patch is preferably left on the skin for a period of at least about 5 minutes, more preferably at least about 15 minutes, more preferably still at least about 30 minutes, even more preferably at least about 1 hour, most preferably at night as a form of night therapy.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Example 1

A skin cream is prepared by conventional methods from the following components.

|  | Ingredient (CTFA Name) | Weight % |
| --- | --- | --- |
| PHASE A: | Water U.S.P. | 53.31 |
|  | Disodium EDTA | 0.13 |
|  | Methyl Paraben | 0.25 |

-continued

|  | Ingredient (CTFA Name) | Weight % |
| --- | --- | --- |
|  | Niacinamide | 2.00 |
|  | Glycerin | 3.00 |
|  | Zinc Citrate | 1.00 |
| PHASE B: | Cetyl Alcohol | 0.56 |
|  | Stearyl Alcohol | 2.03 |
|  | Behenyl Alcohol | 0.22 |
|  | Steareth-21 (Brij 721) | 0.37 |
|  | Steareth-2 (Brij 72) | 1.10 |
|  | Distearyldimonium chloride (Varisoft TA-100) | 0.95 |
|  | Propyl Paraben | 0.10 |
|  | Farnesol | 2.00 |
|  | Polypropylene glycol-15 stearyl ether (Arlamol E) | 3.25 |
| PHASE C: | Polypropylene glycol-15 stearyl ether (Arlamol E) | 2.17 |
|  | Titanium dioxide | 0.75 |
| PHASE D: | Citric acid | 0.19 |
|  | Water U.S.P. | 22.00 |
|  | 50% NaOH | 0.94 |
| PHASE E: | Benzyl Alcohol | 0.50 |
|  | Silicone fluid (DC Q2 - 1401; Cyclomethicone/dimethiconol - 50/50 blend | 0.75 |
|  | Dimethicone 10 cst | 1.00 |
|  | Polyethylene Low Density Beads | 1.00 |
| PHASE F: | Fragrance | 0.10 |
| PHASE G: | 50% NaOH | 0.33 |

Blend the A phase components with a suitable mixer (e.g., Tekmar model RW20DZM), heating while stirring to a temperature of 70–80° C. Separately, blend the B phase components with a suitable mixer and heat with mixing to melt the components. Separately, blend the C phase components and mill to obtain an acceptably smooth mixture (e.g., using a Tekmar T50 Mill).

Add the C phase mixture to the B phase mixture and mix. Then add the resulting mix to the A phase mixture with mixing, cool with a cold water bath and mill, then continue stirring. Remove the combination from the bath, with continued stirring, once the temperature reaches 40° C.

Separately, blend the D phase components by stirring until dissolved, then add this to the combination of A-C materials.

Separately, blend the E phase components by mixing until smooth and continuous, then add this to the combination of the A-D materials. Add and mix the fragrance, then the NaOH. Adjust the pH as necessary to 5.5.

Apply the composition to a subject's intrinsically aged, sagging or photodamaged facial skin at the rate of 2 mg composition/cm² skin once or twice daily for a period of at least 3–6 months to increase skin thickness, reduce red blotchiness and the appearance of spider vessels, reduce sallowness, and diminish skin sagging.

Example 2

An emulsion is prepared by conventional methods from the following components:

| Ingredient | Weight % |
| --- | --- |
| Silicone fluid (Dow Corning DC 345) | 15.0 |
| Silicone fluid (Dow Corning DC 3225C) | 2.50 |
| Silicone fluid (Goldschmidt Abil We09) | 2.50 |
| Water | 71.40 |
| Farnesol | 5.00 |
| Tetrasodium EDTA | 0.10 |

-continued

| Ingredient | Weight % |
|---|---|
| Benzyl alcohol | 0.30 |
| Methyl paraben | 0.20 |
| Glycerin | 3.00 |

Form the water phase in a suitable vessel charged with the water as follows: add the glycerin to the water with stirring. Add to this mixture with stirring the methyl paraben dissolved in the benzyl alcohol. Add to this mixture with stirring the EDTA.

Form the silicone phase in a separate suitable vessel by adding and stirring together the silicone fluids and the farnesol.

Add the water phase to the silicone phase slowly with stirring to form the emulsion.

Apply the resulting composition to a subject's intrinsically aged, sagging or photodamaged facial skin at the rate of 2 mg composition/cm$^2$ skin once or twice daily for a period of at least 3–6 months to increase skin thickness, reduce red blotchiness, and diminish skin sagging.

Example 3

A skin cream is prepared by conventional methods from the following components.

| | Ingredient (CTFA Name) | Weight % |
|---|---|---|
| PHASE A: | Water U.S.P. | 60.96 |
| | Disodium EDTA | 0.15 |
| | Glycerin | 5.00 |
| | Niacinamide | 2.00 |
| PHASE B: | Cetyl hydroxy ethyl cellulose | 0.15 |
| | Methyl Paraben | 0.25 |
| PHASE C: | Cetyl Alcohol | 0.50 |
| | Stearyl Alcohol | 0.50 |
| | Behenyl Alcohol | 0.50 |
| | Cetyl ricinoleate | 3.00 |
| | Steareth-2 (Brij 72) | 1.05 |
| | Distearyldimonium chloride (Varisoft TA-100) | 0.25 |
| | Propyl Paraben | 0.10 |
| | Myristyl myristate | 1.50 |
| | Caprylic/Capritryglycerides | 1.50 |
| | Mineral oil | 2.00 |
| | Farnesol | 1.00 |
| | Fatty acid ester of sugar* | 1.00 |
| | Polypropylene glycol-15 stearyl ether (Arlamol E) | 1.05 |
| PHASE D: | Dimethicone 10 cst (Dow Corning) | 2.00 |
| PHASE E: | Water U.S.P. | 15.00 |
| PHASE F: | Benzyl Alcohol | 0.50 |
| PHASE G: | 50% NaOH | 0.04 |

*A C1–C30 monoester or polyester of sugars and one or more carboxylic acid moieties as described herein, preferably a sucrose polyester in which the degree of esterification is 7–8, and in which the fatty acid moieties are C18 mono- and/or di-unsaturated and behenic acids, in a molar ratio of unsaturates:behenic acid of 1:7 to 3:5, more preferably the octaester of sucrose in which there are about 7 behenic fatty acid moieties and about 1 oleic acid moiety in the molecule, e.g., sucrose ester of cottonseed oil fatty acids.

Blend the A phase components with a suitable mixer (e.g., Tekmar model RW20DZM), heating while stirring to a temperature of about 70–80° C. Add the cetyl hydroxy ethyl cellulose and methyl paraben with mixing at about 70–80° C. to melt the components. Separately, blend the C phase components and mill to obtain an acceptably smooth mixture (e.g., using a Tekmar T50 Mill).

Add the C phase mixture to the above mixture and mix. Remove the combination from the bath, with continued stirring, once the temperature reaches about 45° C. Add the dimethicone and mix.

Separately, blend the E phase components by mixing until smooth and continuous, then add this to the above mixture. Add and mix in the benzyl alcohol, then the NaOH. Adjust the pH as necessary to 7.

Apply the composition to a subject's intrinsically aged, sagging or photodamaged facial skin at the rate of 2 mg composition/cm$^2$ skin once or twice daily for a period of at least 3–6 months to increase skin thickness, reduce red blotchiness, diminish under-eye circles, soften/smooth lips, and diminish skin sagging.

Example 4

A skin cream is prepared by conventional methods from the following components.

| | Component | Weight % |
|---|---|---|
| PHASE A: | Benzyl alcohol | 0.30 |
| | Methyl p-hydroxybenzoate (a.k.a. methylparaben) | 0.20 |
| | Ethanol | 3.00 |
| PHASE B: | Water | 59.60–60.35 |
| | Disodium EDTA | 0.50 |
| | Glycerol | 10.00 |
| | Hexylene glycol | 2.00 |
| | Triethanol amine | 0.05 |
| | Butylated hydroxytoluene | 0.10 |
| PHASE C: | Dow Corning 345 Fluid | 12.50 |
| | Abil WE-09 | 2.50 |
| | Dow Corning -3225C | 2.50 |
| | Petrolatum | 1.50 |
| | Farnesol | 1.00 |
| | Unsubstituted flavanone | 1.00 |
| | Retinol (10% in soybean oil) | 0.75–1.50 |
| | Fatty acid ester of sugar* | 1.00 |

*See Example 3

Blend the A phase components with a suitable mixer (e.g., Tekmar model RW20DZM). Blend the B phase components into the A phase with a suitable mixer. Separately, blend the C phase components until they are uniform. Add the C phase mixture to the A/B phase mixture, mix until uniform and emulsified, and then mill to obtain an acceptably smooth mixture (e.g., using a Tekmar T50 Mill).

Apply the composition to a subjects intrinsically aged, sagging, or photodamaged facial skin at the rate of 2 mg composition/cm$^2$ skin once or twice daily for a period of at least 3–6 months to increase skin thickness, reduce red blotchiness and the appearance of spider vessels, relieve skin itch, and diminish skin sagging.

An alternative skin cream having reduced retinol levels can be prepared in the same manner from the above components wherein the retinol is added in an amount of 0.025% (0.25% of 10% retinol in soybean oil), quo sine to 100% with water, the amounts of the other components being as shown.

While particular embodiments of the subject invention have been described, it will be obvious to those skilled in the art that various changes and modifications to the subject invention can be made without departing from the spirit and scope of the invention. It is intended to cover, in the appended claims, all such modifications that are within the scope of the subject invention.

What is claimed is:

1. A method of regulating the condition of mammalian keratinous tissue, said method comprising the step of topically applying to the keratinous tissue of a mammal in need of such regulation, a safe and effective amount of a composition comprising:
   a) a safe and effective amount of a keratinous tissue condition regulating agent consisting essentially of farnesol; and
   b) a dermatologically-acceptable carrier for the regulating agent.

2. The method of claim 1 wherein the composition comprises from about 0.001% to about 100%, by weight of the composition, of farnesol.

3. The method of claim 1 wherein said composition additionally comprises a safe and effective amount of a skin care active other than farnesol, selected from the group consisting of desquamatory actives, anti-acne actives, vitamin $B_3$ compounds, retinoids, peptides, hydroxy acids, anti-oxidants, radical scavengers, chelators, anti-inflammatory agents, topical anesthetics, tanning actives, skin lightening agents, anti-cellulite agents, flavonoids, anti-microbial actives, antifungal actives, sunscreen actives, conditioning agents, structuring agents, thickening agents, and combinations thereof.

4. The method of claim 3 wherein the desquamatory active is cetyl betaine; the vitamin $B_3$ compound is selected from the group consisting of niacinamide, tocopherol nicotinate, and combinations thereof; the retinoid is retinyl propionate, the peptide is a pentapeptide or a derivative thereof; the hydroxy acid is salicylic acid, the anti-oxidant is selected from the group consisting of tocopherol, tocopherol esters, and combinations thereof; the anti-inflammatory agent is selected from the group consisting of bisabolol, phytosterol, and combinations thereof; the flavonoid is isoflavone, the conditioning agent is selected from the group consisting of panthenol, allantoin, and combinations thereof; and combinations thereof.

5. A method of thickening the skin and/or preventing/retarding skin atrophy of a mammal, said method comprising the step of topically applying to the skin of a mammal needing such treatment, a safe and effective amount of a composition comprising:
   a) a safe and effective amount of farnesol; and
   b) a dermatologically-acceptable carrier for the farnesol.

6. The method of claim 5 wherein said composition additionally comprises a safe and effective amount of a skin care active other than farnesol, selected from the group consisting of desquamatory actives, anti-acne actives, vitamin $B_3$ compounds, retinoids, peptides, hydroxy acids, anti-oxidants, radical scavengers, chelators, anti-inflammatory agents, topical anesthetics, tanning actives, skin lightening agents, anti-cellulite agents, flavonoids, anti-microbial actives, antifungal actives, sunscreen actives, conditioning agents, structuring agents, thickening agents, and combinations thereof.

7. The method of claim 6 wherein the desquamatory active is cetyl betaine; the vitamin $B_3$ compound is selected from the group consisting of niacinamide, tocopherol nicotinate, and combinations thereof; the retinoid is retinyl propionate, the peptide is a pentapeptide or a derivative thereof, the hydroxy acid is salicylic acid, the anti-oxidant is selected from the group consisting of tocopherol, tocopherol esters, and combinations thereof; the anti-inflammatory agent is selected from the group consisting of bisabolol, phytosterol, and combinations thereof; the flavonoid is isoflavone, the conditioning agent is selected from the group consisting of panthenol, allantoin, and combinations thereof; and combinations thereof.

8. A method of preventing and/or retarding the appearance of spider vessels and/or red blotchiness on mammalian skin, said method comprising the step of topically applying to the skin of a mammal needing such treatment, a safe and effective amount of a composition comprising:

a) a safe and effective amount of farnesol; and b) a dermatologically-acceptable carrier for the farnesol.

9. The method of claim 8 wherein said composition additionally comprises a safe and effective amount of a skin care active other than farnesol, selected from the group consisting of desquamatory actives, anti-acne actives, vitamin $B_3$ compounds, retinoids, peptides, hydroxy acids, anti-oxidants, radical scavengers, chelators, anti-inflammatory agents, topical anesthetics, tanning actives, skin lightening agents, anti-cellulite agents, flavonoids, anti-microbial actives, antifungal actives, sunscreen actives, conditioning agents, structuring agents, thickening agents, and combinations thereof.

10. The method of claim 9 wherein the desquamatory active is cetyl betaine; the vitamin $B_3$ compound is selected from the group consisting of niacinamide, tocopherol nicotinate, and combinations thereof; the retinoid is retinyl propionate, the peptide is a pentapeptide or a derivative thereof, the hydroxy acid is salicylic acid, the anti-oxidant is selected from the group consisting of tocopherol, tocopherol esters, and combinations thereof; the anti-inflammatory agent is selected from the group consisting of bisabolol, phytosterol, and combinations thereof; the flavonoid is isoflavone, the conditioning agent is selected from the group consisting of panthenol, allantoin, and combinations thereof; and combinations thereof.

11. A method of preventing and/or retarding the appearance of dark circles on the skin under the eye of a mammal, said method comprising the step of topically applying to the skin surrounding the eye of a mammal needing such treatment, a safe and effective amount of a composition comprising:

a) a safe and effective amount of farnesol; and b) a dermatologically-acceptable carrier for the farnesol.

12. The method of claim 11 wherein said composition additionally comprises a safe and effective amount of a skin care active other than farnesol, selected from the group consisting of desquamatory actives, anti-acne actives, vitamin $B_3$ compounds, retinoids, peptides, hydroxy acids, anti-oxidants, radical scavengers, chelators, anti-inflammatory agents, topical anesthetics, tanning actives, skin lightening agents, anti-cellulite agents, flavonoids, anti-microbial actives, antifungal actives, sunscreen actives, conditioning agents, structuring agents, thickening agents, and combinations thereof.

13. The method of claim 12 wherein the desquamatory active is cetyl betaine; the vitamin $B_3$ compound is selected from the group consisting of niacinamide, tocopherol nicotinate, and combinations thereof; the retinoid is retinyl propionate, the peptide is a pentapeptide or a derivative thereof, the hydroxy acid is salicylic acid, the anti-oxidant is selected from the group consisting of tocopherol, tocopherol esters, and combinations thereof; the anti-inflammatory agent is selected from the group consisting of bisabolol, phytosterol, and combinations thereof; the flavonoid is isoflavone, the conditioning agent is selected from the group consisting of panthenol, allantoin, and combinations thereof; and combinations thereof.

14. A method of preventing and/or retarding sallowness of mammalian skin, said method comprising the step of topically applying to mammalian skin needing such treatment, a safe and effective amount of a composition comprising:

a) a safe and effective amount of farnesol; and b) a dermatologically-acceptable carrier for the farnesol.

15. The method of claim 14 wherein said composition additionally comprises a safe and effective amount of a skin care active other than farnesol, selected from the group consisting of desquamatory actives, anti-acne actives, vitamin $B_3$ compounds, retinoids, peptides, hydroxy acids, anti-oxidants, radical scavengers, chelators, anti-inflammatory agents, topical anesthetics, tanning actives, skin lightening agents, anti-cellulite agents, flavonoids, anti-microbial actives, antifungal actives, sunscreen actives, conditioning agents, structuring agents, thickening agents, and combinations thereof.

16. The method of claim 15 wherein the desquamatory active is cetyl betaine; the vitamin $B_3$ compound is selected from the group consisting of niacinamide, tocopherol nicotinate, and combinations thereof; the retinoid is retinyl propionate, the peptide is a pentapeptide or a derivative thereof, the hydroxy acid is salicylic acid, the anti-oxidant is selected from the group consisting of tocopherol, tocopherol esters, and combinations thereof; the anti-inflammatory agent is selected from the group consisting of bisabolol, phytosterol, and combinations thereof; the flavonoid is isoflavone, the conditioning agent is selected from the group consisting of panthenol, allantoin, and combinations thereof; and combinations thereof.

17. A method of preventing and/or retarding sagging of mammalian skin, said method comprising, the step of topically applying to the skin of a mammal needing such treatment, a safe and effective amount of a composition comprising:

a) a safe and effective amount of farnesol; and b) a dermatologically-acceptable carrier for the farnesol.

18. The method of claim 17 wherein said composition additionally comprises a safe and effective amount of a skin care active other than farnesol, selected from the group consisting of desquamatory actives, anti-acne actives, vitamin $B_3$ compounds, retinoids, peptides, hydroxy acids, anti-oxidants, radical scavengers, chelators, anti-inflammatory agents, topical anesthetics, tanning actives, skin lightening agents, anti-cellulite agents, flavonoids, anti-microbial actives, antifungal actives, sunscreen actives, conditioning agents, structuring agents, thickening agents, and combinations thereof.

19. The method of claim 18 wherein the desquamatory active is cetyl betaine; the vitamin $B_3$ compound is selected from the group consisting of niacinamide, tocopherol nicotinate, and combinations thereof; the retinoid is retinyl propionate, the peptide is a pentapeptide or a derivative thereof, the hydroxy acid is salicylic acid, the anti-oxidant is selected from the group consisting of tocopherol, tocopherol esters, and combinations thereof; the anti-inflammatory agent is selected from the group consisting of bisabolol, phytosterol, and combinations thereof; the flavonoid is isoflavone, the conditioning agent is selected from the group consisting of panthenol, allantoin, and combinations thereof; and combinations thereof.

20. A method of softening and/or smoothing lips, hair and nails of a mammal, said method comprising the step of topically applying to the lips, hair, and nails of a mammal needing such treatment, a safe and effective amount of a composition comprising:

a) a safe and effective amount of a softening/smoothing agent consisting essentially of farnesol; and b) a dermatologically-acceptable carrier for the softening/smoothing agent.

21. The method of claim 20 wherein said composition additionally comprises a safe and effective amount of a skin care active other than farnesol, selected from the group consisting of desquamatory actives, anti-acne actives, vitamin $B_3$ compounds, retinoids, peptides, hydroxy acids, anti-oxidants, radical scavengers, chelators, anti-inflammatory agents, topical anesthetics, tanning actives, skin lightening agents, anti-cellulite agents, flavonoids, anti-microbial actives, antifungal actives, sunscreen actives, conditioning agents, structuring agents, thickening agents, and combinations thereof.

22. The method of claim 21 wherein the desquamatory active is cetyl betaine; the vitamin $B_3$ compound is selected from the group consisting of niacinamide, tocopherol nicotinate, and combinations thereof; the retinoid is retinyl propionate, the peptide is a pentapeptide or a derivative thereof, the hydroxy acid is salicylic acid, the anti-oxidant is selected from the group consisting of tocopherol, tocopherol esters, and combinations thereof; the anti-inflammatory agent is selected from the group consisting of bisabolol, phytosterol, and combinations thereof; the flavonoid is isoflavone, the conditioning agent is selected from the group consisting of panthenol, allantoin, and combinations thereof; and combinations thereof.

23. A method of preventing and/or relieving itch of mammalian skin, said method comprising the step of topically applying to the skin of a mammal needing such treatment, a safe and effective amount of a composition comprising:

a) a safe and effective amount of farnesol; and b) a dermatologically-acceptable carrier for the farnesol.

24. The method of claim 23 wherein said composition additionally comprises a safe and effective amount of a skin care active other than farnesol, selected from the group consisting of desquamatory actives, anti-acne actives, vitamin $B_3$ compounds, retinoids, peptides, hydroxy acids, anti-oxidants, radical scavengers, chelators, anti-inflammatory agents, topical anesthetics, tanning actives, skin lightening agents, anti-cellulite agents, flavonoids, anti-microbial actives, antifungal actives, sunscreen actives, conditioning agents, structuring agents, thickening agents, and combinations thereof.

25. The method of claim 24 wherein the desquamatory active is cetyl betaine; the vitamin $B_3$ compound is selected from the group consisting of niacinamide, tocopherol nicotinate, and combinations thereof; the retinoid is retinyl propionate, the peptide is a pentapeptide or a derivative thereof, the hydroxy acid is salicylic acid, the anti-oxidant is selected from the group consisting of tocopherol, tocopherol esters, and combinations thereof; the anti-inflammatory agent is selected from the group consisting of bisabolol, phytosterol, and combinations thereof; the flavonoid is isoflavone, the conditioning agent is selected from the group consisting of panthenol, allantoin, and combinations thereof; and combinations thereof.

* * * * *

UNITED STATES PATENT AND TRADEMARK OFFICE
CERTIFICATE OF CORRECTION

PATENT NO. : 6,284,802 B1
DATED : September 4, 2001
INVENTOR(S) : D.L. Bissett et al.

It is certified that error appears in the above-identified patent and that said Letters Patent is hereby corrected as shown below:

Column 14,
Line 40, "*Technology*" should read -- *Technology*, --.

Column 18,
Line 57, "$1 \times 10^{31\ 6}\%$" should read -- $1 \times 10^{6}\%$ --.

Column 20,
Line 5, "flavanones" should read -- flavones --.

Column 25,
Line 2, "p-amninobenzoic" should read -- p-aminobenzoic --.

Column 32,
Line 48, "subjects" should read -- subject's --.

Signed and Sealed this

Tenth Day of June, 2003

JAMES E. ROGAN
*Director of the United States Patent and Trademark Office*